(12) United States Patent
Benefield et al.

(10) Patent No.: US 10,685,585 B2
(45) Date of Patent: Jun. 16, 2020

(54) PHYSICAL ACTIVITY AND DIETARY BASED SERVICES

(71) Applicant: International Business Machines Corporation, Armonk, NY (US)

(72) Inventors: Stuart B. Benefield, Durham, NC (US); Samuel R. Connor, Apex, NC (US); Jonathan W. Jackson, Cedar Grove, NC (US); Joseph P. Kuczynski, North Port, FL (US)

(73) Assignee: International Business Machines Corporation, Armonk, NY (US)

(*) Notice: Subject to any disclaimer, the term of this patent is extended or adjusted under 35 U.S.C. 154(b) by 344 days.

(21) Appl. No.: 15/634,315

(22) Filed: Jun. 27, 2017

(65) Prior Publication Data

US 2018/0374385 A1 Dec. 27, 2018

(51) Int. Cl.
*G09B 19/00* (2006.01)
*A63B 71/06* (2006.01)
(Continued)

(52) U.S. Cl.
CPC ...... *G09B 19/0092* (2013.01); *A61B 5/14532* (2013.01); *A61B 5/157* (2013.01); *A63B 24/0059* (2013.01); *A63B 24/0062* (2013.01); *A63B 71/0686* (2013.01); *G06Q 10/087* (2013.01); *G06Q 30/0282* (2013.01); *G06Q 50/12* (2013.01); *A61B 5/4866* (2013.01); *A61B 5/4872* (2013.01); *A63B 2220/12* (2013.01); *A63B 2220/17* (2013.01); *A63B 2220/20* (2013.01); *A63B 2220/40* (2013.01);
(Continued)

(58) Field of Classification Search
CPC . G09B 19/0092; A61B 5/14532; A61B 5/157; A63B 24/0059; A63B 24/0062; A63B 71/0686; G06Q 50/12; G06Q 10/087; G06Q 30/0282
USPC ........................................................ 434/127
See application file for complete search history.

(56) References Cited

U.S. PATENT DOCUMENTS 7,172,530 B1  2/2007 Hercules
8,690,578 B1  4/2014 Nusbaum
(Continued)

FOREIGN PATENT DOCUMENTS

CN   105147021 A   12/2015
KR   1020070045434 A   5/2007
TW   200905596 A   2/2009

OTHER PUBLICATIONS

Benefield et al., "Physical Activity and Dietary Based Services", U.S. Appl. No. 15/783,532, filed Oct. 13, 2017, 60 pages.
(Continued)

*Primary Examiner* — Robert P Bullington
(74) *Attorney, Agent, or Firm* — Donald G. Weiss

(57) ABSTRACT

In an approach for providing dynamic services a computer receives a dietary plan for an individual. The computer tracks physical activity data for the individual. The computer creates one or more propositions for the individual based at least in part on the received dietary plan and the tracked physical activity data. The computer provides the created one or more propositions to the individual. The computer receives a selection from the created one or more propositions. The computer tracks the received selection.

14 Claims, 3 Drawing Sheets

(51) Int. Cl.
*G06Q 50/12* (2012.01)
*A61B 5/145* (2006.01)
*A61B 5/157* (2006.01)
*G06Q 10/08* (2012.01)
*A63B 24/00* (2006.01)
*G06Q 30/02* (2012.01)
*A61B 5/00* (2006.01)

(52) U.S. Cl.
CPC ....... *A63B 2220/73* (2013.01); *A63B 2220/74* (2013.01); *A63B 2220/803* (2013.01); *A63B 2220/836* (2013.01); *A63B 2230/06* (2013.01)

(56) References Cited

U.S. PATENT DOCUMENTS

| | | |
|---|---|---|
| 8,799,083 B1 | 8/2014 | Silver |
| 9,514,655 B1 | 12/2016 | Nusbaum et al. |
| 2012/0094258 A1 | 4/2012 | Langheier et al. |
| 2013/0280681 A1 | 10/2013 | Narayan et al. |
| 2014/0164013 A1 | 6/2014 | Schwarzberg et al. |
| 2014/0287384 A1* | 9/2014 | Boyes ................ G06F 19/3475 434/127 |
| 2014/0335490 A1* | 11/2014 | Baarman ................ A61B 5/002 434/236 |
| 2014/0377725 A1 | 12/2014 | Kidron et al. |
| 2016/0071423 A1 | 3/2016 | Sales |
| 2018/0075218 A1 | 3/2018 | Benefield |

OTHER PUBLICATIONS

Appendix P, List of IBM Patents or Patent Applications Treated as Related, 2 pages, dated Oct. 18, 2017.

Bort, Julie, "MyFitnessPal can now help you find a restaurant based on how many calories you want to eat", Business Insider, Jan. 8, 2016, 8 pages, Copyright © 2017 Business Insider Inc., <http://www.businessinsider.com/myfitnesspal-now-logs-restaruant-meals-2016-1>.

"Free Custom Fitness Meal Planner", Scooby's Workshop, ©2015 scoobysworkshop.com llc, 2 pages, <http://custommealplanner.com>.

"System and Method for Monitoring Health and Selecting Appropriate Restaurant Menu Item", An IP.com Prior Art Database Technical Disclosure, Authors et. al.: Disclosed Anonymously, IP.com Number: IPCOM000242901D, IP.com Electronic Publication Date: Aug. 28, 2015, 4 pages.

* cited by examiner

PHYSICAL ACTIVITY AND DIETARY BASED SERVICES

BACKGROUND

The present invention relates generally to the field of exercise and nutrition and more particularly to dynamically provide services based on physical activity and dietary goals.

Regular exercise (e.g., physical activity) is a component of good physical and mental health as well as a means for weight control. Exercise burns fat, builds muscle, lowers cholesterol, eases stress and anxiety, allows for restful sleep, etc. Individuals perform exercise consciously and unconsciously through a variety of activities such as housework, running, swimming, walking, biking, weight lifting, etc. The reasons for which an individual performs exercise varies based on personal goals and/or reasons (e.g., weight loss, weight maintenance, stress relief, health considerations, fitness goals, etc.). In order to achieve personal goals and a healthy lifestyle, individuals incorporate nutrition and calorie control with exercise.

In order to carry out daily activities individuals ingest food, which provides energy in the form of calories. Each age group and gender require a different amount of calories from each type of food energy or fuel type (i.e., fat, protein, and carbohydrates) to maintain proper bodily function. In addition, the size of the individual (e.g., height and weight), goals, the time spent performing the physical activity, type of physical activity, and activity level (e.g., light, moderate, very active, extremely active, etc.) also alters the number of calories an individual should consume. The individual maintains, gains, or loses body weight based on an energy balance between the food eaten and energy expended by basic body functions (e.g., temperature, heart rate, breathing, etc.) and physical activity.

Fitness trackers (e.g., physical activity tracker) are devices and/or applications that monitor and track fitness-related metrics such as distance, heartbeat, quality of sleep, type of activity, length of activity, etc. Fitness trackers measure an individual's heartbeat through a fitted chest strap, an optical sensor, and/or another sensor (e.g., biometric). The fitted chest strap includes electrodes, which are in contact with the individual's skin. When the individual's heart beats, a small electrical signal is sent through the heart muscles, which causes a contraction (e.g., one heartbeat). The electrodes detect the electrical signal and send the detection to a microprocessor for monitoring and calculation of the individual's heart rate. Optical sensors work by shining a light on the skin of the individual. The light illuminates capillaries and the optical sensor measures the rate at which blood is being pumped through the capillaries, and thus determines a heart rate. In order to track physical activity, fitness trackers include a 3-axis accelerometer to track movement in each direction, and a gyroscope to measure orientation and rotation. Software associated with the fitness trackers utilize personal data (e.g., height, weight, age, stride length, etc.) with the collected sensor data to convert the movement into steps and activity in addition to calculating a number of calories expended by the individual to perform the activity.

SUMMARY

Aspects of the present invention disclose a method, computer program product, and system for providing dynamic services, the method comprises one or more computer processors receiving a dietary plan for an individual. The method further comprises one or more computer processors tracking physical activity data for the individual. The method further comprises one or more computer processors creating one or more propositions for the individual based at least in part on the received dietary plan and the tracked physical activity data. The method further comprises one or more computer processors providing the created one or more propositions to the individual. The method further comprises one or more computer processors receiving a selection from the created one or more propositions. The method further comprises one or more computer processors tracking the received selection.

DETAILED DESCRIPTION

Figure 1:
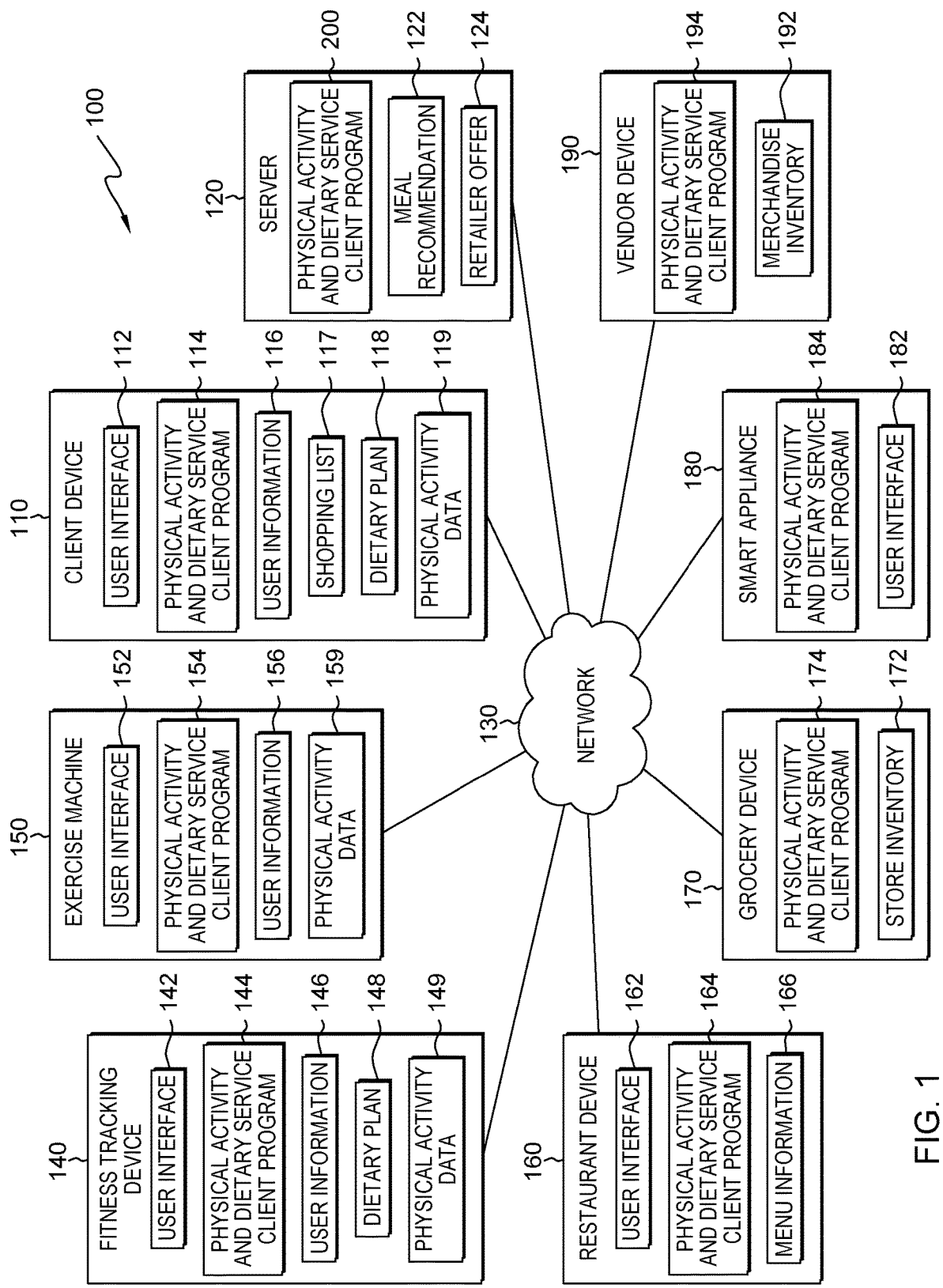
FIG. 1 is a functional block diagram illustrating a distributed data processing environment, in accordance with an embodiment of the present invention.

Physical activity (e.g., exercise) and nutrition assist individuals in obtaining and maintaining physical wellbeing and a healthy lifestyle. Embodiments of the present invention recognize that individuals attempting to achieve and/or maintain physical wellbeing and a healthy lifestyle follow exercise and/or dietary plans to reach set goals (e.g., weight loss, weight maintenance, building of muscle mass, etc.) and/or for specific health reasons (e.g., diabetes, cholesterol, high blood pressure, etc.). Embodiments of the present invention recognize that to achieve the goals and/or health benefits, individuals create food plans and manually track calories consumed through food intake and calories burned through physical activity in order to track progress. However, embodiments of the present invention recognize that food plans do not assist the individuals in making consumption decisions at mealtime and/or between meals that are based on activity level and a nutritional composition of foods and beverages consumed over a period of time (e.g., a period of hours, time between meals, 24 hour period, a set number of hours proceeding a workout, a set number of hours following a workout, etc.) to receive a maximum benefit and/or to maintain goals. Additionally embodiments of the present invention recognize that retailers (e.g., sellers and/or service providers) of food, nutritional supplements, and/or physical activity equipment are currently unable to provide dynamic and/or real-time customized service to individuals based on actual physical activity and/or dietary goals of the individuals.

Embodiments of the present invention incorporate physical activity tracking with dietary and nutritional plans to assist individuals to meet goals, restrictions, and/or conditions (e.g., physical, dietary, and/or medical). Embodiments of the present invention track calorie consumption and/or food energy consumed (i.e., types of calories and nutritional content consumed by an individual as, proteins, fats, carbohydrates, etc.) in conjunction with performed physical activity for a time period for the individuals. Embodiments of the present invention balance and adjust dietary options for individuals that coincide with a total number of remaining calories allowed (i.e., tracks consumption and adjusts in real time), types of food energy and nutrients to consume based on the dietary plan and the type of physical activity performed by the individuals (e.g., cardio, weight lifting, aerobic, etc.). Embodiments of the present invention interface with retailers, thereby allowing use of an individual's user data (e.g., calories allowed, physical activity performed, nutritional considerations, preferences, restrictions, etc.) to provide dynamic real time meal options, services, products, and/or rewards that assist the individual to meet goals and achieve physical wellbeing and a healthy lifestyle. Embodiments of the present invention aid in building and fostering brand loyalty between the individuals and the service providers, as the tailored services, recommendations (e.g., proposition, offer, etc.), and rewards support and motivate individuals to reach goals, thereby creating positive connotations.

The present invention will now be described in detail with reference to the Figures. FIG. 1 is a functional block diagram illustrating a distributed data processing environment, generally designated 100, in accordance with one embodiment of the present invention. FIG. 1 provides only an illustration of one embodiment and does not imply any limitations with regard to the environments in which different embodiments may be implemented.

In the depicted embodiment, distributed data processing environment 100 includes client device 110, server 120, fitness tracking device 140, exercise machine 150, restaurant device 160, grocery device 170, smart appliance 180, and vendor device 190 interconnected over network 130. Distributed data processing environment 100 may include additional computing devices, mobile computing devices, servers, computers, storage devices, or other devices not shown.

Client device 110 may be a web server or any other electronic device or computing system capable of processing program instructions and receiving and sending data. In some embodiments, client device 110 may be a laptop computer, a tablet computer, a netbook computer, a personal computer (PC), a desktop computer, a personal digital assistant (PDA), a smart phone, or any programmable electronic device capable of communicating with network 130. In other embodiments, client device 110 may represent a server computing system utilizing multiple computers as a server system, such as in a cloud computing environment. In some other embodiment, client device 110 includes a global positioning system chip that provides location data. In one embodiment, client device 110 includes application software that connects client device 110 and fitness tracking device 140 in order to send and receive information. For example, fitness tracking device 140 uploads physical activity data 149 (e.g., adds activity to physical activity data 119 and/or replaces a duplicate activity), steps taken, heart rate, and calories burned to client device 110 for tracking within an application and/or by physical activity and dietary service client program 114. In another embodiment, client device 110 includes basic physical activity tracking functions (e.g., pedometer) and records steps taken by the individual. In some other embodiment, client device 110 allows for a user to input physical activity, calories burned, heart rate data, etc., manually (e.g., individual enters data) and/or through an upload function, from a portable memory device (e.g., Universal Serial Bus (USB)). For example, a basic pedometer or a heart rate monitor (e.g., combined watch and heart rate monitor) includes a USB connection, that the individual connects to client device 110 and transfers physical activity data 149 from fitness tracking device 140. In another example, an individual connects a USB memory device to an exercise machine 150 and transfers physical activity data 159 from the USB memory stick to client device 110. Client device 110 contains user interface 112, physical activity and dietary service client program 114, user information 116, shopping list 117, dietary plan 118, and physical activity data 119.

Fitness tracking device 140 is a physical activity tracking device. Fitness trackers (e.g., physical activity tracker) are devices and/or applications that monitor and track fitness-related metrics pertaining to physical activity such as distance, heartbeat, quality of sleep, type of activity, length of activity, etc. In one embodiment, fitness tracking device 140 is an upgraded version of a pedometer, that in addition to counting steps, utilizes accelerometers, altimeters, and gyroscopes to calculate mileage, graph overall physical activity, and calculates calorie expenditure. In another embodiment, fitness tracking device 140 monitors and graphs a heart rate and quality of sleep for the individual. Fitness tracking device 140 measures an individual's heartbeat through a fitted chest strap, an optical sensor, and/or another sensor (e.g., biometric). The fitted chest strap includes electrodes, which are in contact with the individual's skin. When the individual's heart beats, a small electrical signal is sent through the heart muscles, which the electrodes detect and utilize for monitoring and calculation of the individual's heart rate. Optical sensors shine a light to illuminate capillaries under the skin, and the optical sensor measures the rate at which blood is pumped through the capillaries to determine the heart rate.

In some other embodiment, fitness tracking device 140 includes a global positioning system. Fitness tracking device 140 includes a system that utilizes satellites in order to provide autonomous geo-spatial positioning. Small electronic receivers within fitness tracking device 140 determine location (longitude, latitude, and altitude/elevation) to high precision using time signals transmitted along a line of sight from satellites. Fitness tracking device 140 can be used for providing position, navigation or for tracking the position of something fitted with a receiver. For example, fitness tracking device 140 includes navigation and tracking capabilities to guide an individual, map a route, and/or track the route the individual creates by using the GPS plus an altimeter, barometer and compass sensor capabilities. A built-in altimeter provides elevation data to monitor ascent and descent. A barometer predicts weather changes by showing short-term trends in air pressure. An electronic compass provides bearing data. Additionally physical activity and dietary service program 200 utilizes the GPS capabilities of fitness tracking device 140 to determine distance and speed associated with a physical activity. For example, physical activity and dietary service program 200 identifies a speed of four miles per hour as a walking activity, as opposed to speed of eight miles per hour, which is a running activity.

In another embodiment, fitness tracking device 140 includes medical monitoring capabilities (e.g., class II medical monitor). A Class II medical device is a medical device for diagnostic and/or therapeutic purposes, in which general controls alone cannot assure safety and effectiveness, and existing methods are available that provide such assurances. In some embodiments, fitness tracking device 140 includes capabilities to analyze a blood sample for a blood sugar level, receive a blood sugar level from a separate blood sampling device, manually receive a blood sugar level, and/or receive a blood sugar profile. Fitness tracking device 140 stores and tracks the blood sugar levels with medication (e.g., insulin treatments), meals, and/or physical activity (e.g., exercise) etc. as a table of blood sugar levels (e.g., blood glucose profile), as measurements are taken over the day and/or days to identify trends and patterns over time for incorporation in dietary plan 148 and to assist the individual to control sugar and/or insulin levels based on the patterns. For example physical activity and dietary service program 200 identifies low blood sugar occurs repeatedly after a specific workout. Therefore, physical activity and dietary service program 200, via user interface 142 suggests the individual check blood sugar levels after the workout and/or consume a snack. In yet some other embodiment, fitness tracking device 140 includes one or more of the aforementioned embodiments.

In some embodiments, fitness tracking device 140 utilizes user information 146 (e.g., height, weight, age, stride length, health information, etc.), and the collected sensor data (e.g., duration of activity, GPS data, speed from the accelerometer, etc.) to convert the movements into steps and physical activity. Additionally, physical activity and dietary service program 200 utilizes heart rate, intensity levels, physical activity data 149, and/or user information to calculate a number of calories burned (e.g., expended by the individual to perform the activity). Fitness tracking device 140 contains user interface 142, physical activity and dietary service client program 144, user information 146, dietary plan 148, and physical activity data 149.

Exercise machine 150 is a machine used during physical activity to enhance the strength or conditioning effects of that exercise by providing either fixed or adjustable amounts of resistance, or to otherwise enhance the experience or outcome of an exercise routine (e.g., stationary bicycle, treadmill, rowing machines, etc.) Exercise machine 150 includes an ergometer, which measures the work a person exerts while exercising. In some embodiments, exercise machine 150 receives user information 156 and/or selection of an exercise program through user interface 152. Exercise machine 150 measures workload intensity and with programmed equations, and the weight of the individual (e.g., weight is entered within user information 156), exercise machine 150 calculates exercise calories (e.g., burned calories, expended calories). Exercise machine 150 controls and tracks the time (e.g., duration of exercise), speed, and intensity level at which an individual performs physical activity from which with a weight, the number of calories expended are calculated. In some embodiments, exercise machine 150 includes heart rate sensors, and/or connects via network 130 to fitness tracking device 140 which provides heart rate information. In some other embodiments, exercise machine 150 includes a user login for tracking, storing, and/or sharing physical activity data 159 associated with the individual. For example at a fitness club (e.g., gym) exercise machine 150 includes a login screen that allows the user to log into an account associated with the individual. By connecting to the account of the individual, exercise machine 150 accesses a separate computer (not shown) that stores user information 156 and uploads physical activity data 159 for one or more individuals to physical activity and dietary service program 200 without requiring the individual to own and/or have fitness tracking device 140, client device 110, present at the time the individual performs physical activity to utilize the benefits of physical activity and dietary service program 200.

Restaurant device 160 is a computing device at an eating establishment (e.g., diner, restaurant, fast food restaurant, coffee shop, donut shop, etc.) that provides information, meal recommendation 122, and/or retailer offer 124 (e.g., discounts) to an individual user based on dietary plan 118 and physical activity data 119 or dietary plan 148 and physical activity data 149. Additionally, restaurant device 160 records a meal selection and sends menu information 166 to fitness tracking device 140 and/or client device 110. Menu information 166 includes the caloric value and nutritional content associated with individual food selections that an individual is able to order off of a predefined menu, which are prepared and/or served at a restaurant and/or food service provider (e.g., list of food and/or beverage that includes prices, calories, and nutritional content that the individual may order from.) For example, a breakfast sandwich is 300 total calories, which includes 12 g of fat, 29 g of carbohydrates, and 18 g of protein.

In one embodiment, restaurant device 160 is a table top computing device that allows customers to view and/or order food from the menu, and also dynamically provides meal recommendation 122 with nutritional and calorie information to the individual prior to ordering. In another embodiment, restaurant device 160 is a drive up menu board and/or an order screen, which dynamically updates by adding meal recommendation 122 that coincides with dietary plan 118 and physical activity data 119 or dietary plan 148 and physical activity data 149. In some embodiments, restaurant device 160 is a computing device utilized by a server to provide meal recommendation 122 to the patron based on dietary plan 118 and physical activity data 119 or dietary plan 148 and physical activity data 149 to enhance the personal experience. For example, the server is notified of the patron's goal to lower cholesterol, and therefore the server recommends a broiled salmon special instead of a salmon in a heavy cream sauce from the menu. In the depicted embodiment, restaurant device 160 includes user interface 162 and menu information 166. Restaurant device 160 sends and receives information to and from, physical activity and dietary service client program 114, physical activity and dietary service client program 144, and/or physical activity and dietary service program 200.

Grocery device 170 is a computing device associated with a grocery store, which assists the individual to identify food items within store inventory 172 for purchase that meet the goals set within dietary plan 118 or dietary plan 148. Store inventory 172 includes food items carried by the grocery store with nutritional and calorie content. In some embodiments, store inventory 172 also includes a location of the identified food items within the grocery store in order to direct the individual to the food item and/or to prompt the user to view the food item when in proximity (e.g., walks down the aisle with the recommended food item, enter the department associated with the food item, etc.). In one embodiment, grocery device 170 is a portable computing device that the user carries through the grocery store, which assists the user while shopping by identifying food items to purchase. For example, physical activity and dietary service program 200 identifies and provides a listing of recommended foods for possible selection from store inventory 172 and notifies the user through audio sounds and/or haptic feedback (e.g., vibration) when nearing a recommended food item through grocery device 170. In another embodiment, grocery device 170 is a centrally located computing device which connects to fitness tracking device 140 and/or client device 110 via physical activity and dietary service program 200 and/or physical activity and dietary service client program 174. Grocery device 170 via physical activity and dietary service client program 174 sends meal recommendation 122 (i.e., identifies foods to purchase) that may be automatically added and/or confirmed on shopping list 117 and creates retailer offer 124 (e.g., discounts, special sales, etc.), based on store inventory 172 and information provided by shopping list 117 and/or, meal recommendation 122. Grocery device 170 includes store inventory 172. Grocery device 170 sends and receives data via physical activity and dietary service client program 174 to and from physical activity and dietary service program 200.

Smart appliance 180 is a home appliance that is capable of reporting status (e.g., operational status, food contents), providing television shows (e.g., news, cooking shows, fitness shows, etc.) and/or accessing the Internet over network 130. For example, the individual is at the grocery store and does not remember what is in the refrigerator, which is smart appliance 180. Prior to buying milk, eggs, broccoli and chicken, the individual connects to the refrigerator and views the food contents. In some embodiments, based on the information from smart appliance 180, dietary plan 118 and physical activity data 119 or dietary plan 148 and physical activity data 149, and physical activity data 119, physical activity and dietary service program 200 recommends: food items to purchase (e.g., meal recommendation 122), recipes to prepare, snacks to eat, and/or provides food consumption information. Smart appliance 180 includes user interface 182 and physical activity and dietary service client program 184. Smart appliance 180 sends and receives information to and from physical activity and dietary service program 200.

Vendor device 190 is a computing device associated with a merchandise store (e.g., provider, entity, business, brick and mortar store, virtual store front, etc.) that provides goods and/or services. Vendor device 190 identifies products and services within merchandise inventory 192 for purchase that the individual utilizes to perform physical activity and/or to meet the goals set within dietary plan 118 or dietary plan 148. Merchandise inventory 192 includes food supplements, exercise equipment, clothes, shoes, fitness tracking devices, exercise videos, gym memberships, yoga studio classes, personal training services, etc. In one embodiment, physical activity and dietary service program 200 provides retailer offer 124 (e.g., discounts, special sales, etc.) upon detection of client device 110 and/or fitness tracking device 140 (e.g., proximity as determined by GPS, near field communication, physical activity and dietary service client program 114 and/or 144 connects to physical activity and dietary service client program 194 upon entering the store, etc.) in order to encourage the user to purchase of a particular product from a vendor. In another embodiment, physical activity and dietary service program 200 provides discounts, offers, sales, etc. electronically (e.g., e-mail, website coupon, online codes, through physical activity and dietary service client programs 119 and/or 144, etc.) and/or through hard copy (e.g., paper offers) through postal deliveries for immediate and/or future utilization either online and/or by visiting a specified merchandise store.

In some other embodiment, vendor device 190 is a computing device utilized by a vendor employee to customize a shopping experience. For example, an individual is a runner as noted by the activity type within physical activity data 119. Physical activity and dietary service client program 194 and/or physical activity and dietary service program 200 notifies the salesperson via a user interface (not shown) that the customer is a runner. Based on the received information, the salesperson inquires whether the user is a runner and initiates a conversation about treadmills for which retailer offer 124 are available. Continuing the example, the salesperson receives additional information via the user interface that the customer prefers low impact exercise (e.g., exercise that minimizes the force placed on bones and joints). Therefore instead of discussing treadmills, the salesperson alters the discussion to focus on elliptical trainers, which are low impact to personalize the experience for the customer. In the depicted embodiment, vendor device 190 includes merchandise inventory 192 and physical activity and dietary service client program 194. In some embodiments, vendor device 190 also includes a user interface (not shown).

User information 116 and user information 146 are personal data regarding the individual which includes one or more of the following: gender, weight, height, age, stride length, blood glucose profile, heart rate maximum, heart rate minimum, cholesterol levels, blood pressure, medical restrictions, activity restrictions, allergies, injuries, etc. User information 116 and 146 are associated with a specific individual for private use and therefore are permanently stored within memory on client device 110 and fitness tracking device 140. User information 116 and/or 146 are entered at set up and/or may be modified over time as changes occur. In one embodiment user information 116 and user information 146 are the same (e.g., identical information is entered separately, and/or a user selects to upload user information 116 or user information 146 to fitness tracking device 140 or client device 110 respectively). In another embodiment, user information 116 and user information 146 may include variations, such as more or less data fields depending upon the application software and capabilities on the installed device and/or different values if the user entered different data. In the depicted embodiment, user information 116 and user information 146 reside on client device 110 and fitness tracking device 140. In another embodiment, user information 116 and/or user information 146 may reside on server 120 or on another device (not shown) connected over network 130 for utilization by physical activity and dietary service program 200 and/or to be downloaded for utilization on client device 110, fitness tracking device 140, and/or exercise machine 150.

User information 156 includes a subset of personal data pertaining to an individual (e.g., age, weight, and gender), in which, physical activity and dietary service program 200 utilizes age and gender to calculate target heart rate zones and utilizes weight to calculate calories expended. For example exercise machine 150 is located in a gym that multiple individuals use. As exercise machine 150 is shared, user information 156 resets to a default between individual users (e.g., maintains user privacy), and requests the user login and/or enter user information 156 upon starting. To avoid delays in beginning an exercise program, physical activity and dietary service client program 154 requests minimal personal data from the individual to calculate calories burned. In one embodiment, the user enters user information 156 for utilization by physical activity and dietary service client program 154. In another embodiment, an individual selects general average user information (e.g., default user settings) as user information 156. For example, a user enters a quick start option on exercise machine 150, which bypasses the option for the individual to enter user information 156. Exercise machine 150 utilizes average user information as user information 156, (e.g., weight is 150 lbs and age is 35). However, by utilizing default user information, errors are introduced into physical activity data 159 as the calories burned may be higher or lower depending upon the actual age and weight of the individual. Physical activity and dietary service client program 154 utilizes user information 156 to calculate the number of calories burned through exercise for further utilization by physical activity and dietary service program 200. In the depicted embodiment, user information 156 resides on exercise machine 150. In another embodiment, user information 156 may reside on server 120 or on another device (not shown) connected over network 130 for utilization by physical activity and dietary service program 200 and/or to be downloaded for utilization on client device 110, fitness tracking device 140, and/or exercise machine 150.

User interface 112 is a program that provides an interface between a user of client device 110, and a plurality of applications that reside on client device 110 (e.g., user information 116, shopping list 117, and dietary plan 148) and/or may be accessed over network 130. User interface 142 is a program that provides an interface between a user of fitness tracking device 140 and a plurality of applications that reside on fitness tracking device 140 (e.g., user information 146, dietary plan 148) and/or may be accessed over network 130. User interface 152 is a program that provides an interface between a user of exercise machine 150 and a plurality of applications that reside on exercise machine 150 (e.g., user information 156) and/or may be accessed over network 130. User interface 162 is a program that provides an interface between a user of restaurant device 160 (e.g., customer, server, etc.) and a plurality of applications that reside on restaurant device 160 (e.g., menu information 166) and/or may be accessed over network 130. User interface 182 is a program that provides an interface between a user of smart appliance 180 and a plurality of applications that reside on smart appliance 180 and/or may be accessed over network 130.

User interfaces, such as user interface 112, user interface 142, user interface 152, user interface 162, and user interface 182 refers to the information (e.g., graphic, text, sound) that a program presents to a user and the control sequences the user employs to control the program. A variety of types of user interfaces exist. In one embodiment, user interface 112, user interface 142, and user interface 152 is a graphical user interface. A graphical user interface (GUI) is a type of interface that allows users to interact with peripheral devices (i.e., external computer hardware that provides input and output for a computing device, such as a keyboard and mouse) through graphical icons and visual indicators as opposed to text-based interfaces, typed command labels, or text navigation. The actions in GUIs are often performed through direct manipulation of the graphical elements. User interface 112, user interface 142, user interface 152, user interface 162, and user interface 182 send and receive information through physical activity and dietary service client program 114, physical activity and dietary service client program 144, physical activity and dietary service client program 154, physical activity and dietary service client program 164, and physical activity and dietary service client program 184 respectively to physical activity and dietary service program 200.

Physical activity and dietary service client program 114, physical activity and dietary service client program 144, physical activity and dietary service client program 154, physical activity and dietary service client program 164, physical activity and dietary service client program 174, physical activity and dietary service client program 184, and physical activity and dietary service client program 194 are a set of one of more programs designed to carry out the operations for a specific application (e.g., local installed application that performs functions of and/or provides information for further utilization by physical activity and dietary service program 200) to assist the individual to perform an activity (e.g., track physical activity, track calories burned, track calories consumed, select food items to eat, receive vendor offers, etc.). Physical activity and dietary service client program 114, physical activity and dietary service client program 144, physical activity and dietary service client program 154, physical activity and dietary service client program 164, physical activity and dietary service client program 174, physical activity and dietary service client program 184, and physical activity and dietary service client program 194 are the same program, but are installed on different devices as depicted in FIG. 1, and therefore may access and implement different functionality (e.g., more or less capabilities) based upon the type of device and the functions available (e.g., heart rate monitoring, pedometer, exercise routines, meal/food ordering, etc.).

For example, physical activity and dietary service client program 114 and physical activity and dietary service client program 144 track physical activity as physical activity data 119 and 149 respectively and access dietary plans 118 and 148 in order to track BMR with respect to calories consumed, calories burned, remaining available calories for consumption, goals, and to provide meal recommendation 122. Physical activity and dietary service client program 154 tracks physical activity as physical activity data 159 (e.g., tracks calories burned, type of activity, etc.). However, as exercise machine 150 is a device on which an individual performs exercise, exercise machine 150 does not access dietary plan 118 or dietary plan 148, or provide meal recommendation 122. Physical activity and dietary service client program 114, physical activity and dietary service client program 144, physical activity and dietary service client program 154, physical activity and dietary service client program 164, physical activity and dietary service client program 174, physical activity and dietary service client program 184, and physical activity and dietary service client program 194 send and receive information to and from physical activity and dietary service program 200.

Shopping list 117 is a list of items for purchase (e.g., food, merchandise, etc.). In one embodiment, shopping list 117 is created by a user. In another embodiment, physical activity and dietary service program 200 creates shopping list 117 based on user information 116, dietary plan 118, physical activity data 119, store inventory 172, smart appliance 180, and/or merchandise inventory 192. In the depicted embodiment, shopping list 117 resides on client device 110. In another embodiment, shopping list 117 resides on fitness tracking device 140, server 120, and/or on another computing device (not shown), provided shopping list 117 is available to the user for utilization and/or physical activity and dietary service program 200.

Dietary plan 118 and dietary plan 148 are dietary and nutritional plans (i.e., tailored eating guidelines to match nutritional and caloric intake) to assist individuals to meet goals, restrictions, and/or conditions (e.g., physical, dietary, and/or medical). For example, dietary plan 118 identifies a number of calories for consumption by the individual and a percentage of each food type (e.g., carbohydrates, fats, proteins, nutritional intake) to consume that will equal the number of calories for consumption. Dietary plan 118 and dietary plan 148 may also include nutritional restrictions (e.g., low sodium, low cholesterol, low fat, food allergies, sugar, etc.). Additionally, dietary plan 118 and dietary plan 148 may also include nutritional requirements (e.g., calcium, iron, folic acid) to assist the individual to consume additional nutrients to overcome a deficiency. Dietary plan 118 and dietary plan 148 are created by the user, physical trainer, a dietician (i.e., an expert in human nutrition and the regulation of diet) and/or physical activity and dietary service program 200 based on goals, restrictions, and/or conditions and for the individual). Dietary plan 118 and dietary plan 148 include the same information but are installed on client device 110 and fitness tracking device 140 for utilization respectively. For example, a user may own fitness tracking device 140 (e.g., portable wearable device) but client device 110 is a desktop computer. In order to maintain goals while away from the home, physical activity and dietary service program 200 utilizes dietary plan 148 and sends information to fitness tracking device 140 via physical activity and dietary service client program 144 for utilization by the individual. In the depicted embodiment dietary plan 118 resides on client device 110 and dietary plan 148 resides on fitness tracking device 140. In another embodiment, dietary plan 118 and dietary plan 148 reside on server 120 or on another device provided dietary plan 118 and dietary plan 148 are accessible by physical activity and dietary service program 200, physical activity and dietary service client program 114 and physical activity and dietary service client program 144.

Physical activity data 119, physical activity data 149, and physical activity data 159, provide information pertaining to exercise performed by an individual. Physical activity data 119, physical activity data 149, and physical activity data 159 include the number of calories burned by an individual, the type of activity, and a duration of the activity. Physical activity data 119 and physical activity data 149 update periodically in real time throughout the day based on user-initiated exercise tracking options and/or background tracking functions of client device 110 and/or fitness tracking device 140 that are specific to an individual that provides an accumulating total (i.e., tracks all physical activity performed by the individual). In some embodiments, physical activity data 119 and physical activity data 149 are the same. For example, a user wears fitness tracking device 140, which the user connects to client device 110 and shares physical activity data 149 over network 130 via physical activity and dietary service client programs 114 and 144. Therefore, physical activity data 119 is a copy of physical activity data 149. Physical activity data 159 is associated with a set period of time for an exercise performed on exercise machine 150 and only represents a portion of physical activity performed by the individual. In some embodiments, physical activity data 119, physical activity data 149, and physical activity data 159 also include heart rate information (e.g., minimum HR, maximum HR, average HR, etc.) steps taken, distance traversed, intensity level, etc.

In some embodiments, physical activity data 119 and physical activity data 149 include physical activity data 159. For example, a user uploads physical activity data 159 to client device 110 and/or fitness tracking device 140 through physical activity and dietary service client program 114 or physical activity and dietary service client program 144. Physical activity data 159 is added to and/or replaces a portion of physical activity data 119 and/or physical activity data 149. For example, an individual utilizes client device 110 that is not a wearable device. Through physical activity and dietary service client program 114, the user adds physical activity data 159 in order to improve the accuracy of recommendations from physical activity and dietary service program 200. In the depicted embodiment, physical activity data 119 resides on client device 110, physical activity data 119 resides on fitness tracking device 140, and physical activity data 159 resides on exercise machine 150. In another embodiment, physical activity data 119, physical activity data 149, and physical activity data 159 reside on server 120 or on another device, provided that physical activity data 119, physical activity data 149, and physical activity data 159 are accessible by physical activity and dietary service program 200, physical activity and dietary service client program 114, physical activity and dietary service client program 144 and physical activity and dietary service client program 154.

Server 120 may be a management server, a web server, or any other electronic device or computing system capable of receiving and sending data. In some embodiments, server 120 may be a laptop computer, a tablet computer, a netbook computer, a personal computer (PC), a desktop computer, a personal digital assistant (PDA), a smart phone, or any programmable device capable of communication with client device 110 over network 130. In other embodiments, server 120 may represent a server computing system utilizing multiple computers as a server system, such as in a cloud computing environment. In general, server 120 is representative of any electronic device or combination of electronic devices capable of executing machine readable program instructions as described in greater detail with regard to FIG. 3, in accordance with embodiments of the present invention. Server 120 contains owner meal recommendation 122, retailer offer 124, and physical activity and dietary service program 200.

Meal recommendation 122 is a meal (e.g., breakfast, lunch, dinner, snack, etc.) and beverage (e.g., water, milk, juice, coffee, tea, soft drinks, hydration, diuretic, etc.) suggestion and/or proposition (i.e., act of offering or suggestion something to be considered, such as a proposed plan or an offer of terms for a transaction), as determined by physical activity and dietary service program 200. In various embodiments, physical activity and dietary service program 200 determines meal recommendations 122 based on a combination of one or more of the following: user information 116, dietary plan 118, physical activity data 119, user information 146, dietary plan 148, physical activity data 149, menu information 166, store inventory 172, and smart appliance 180 (e.g., determines food and beverage suggestions based on nutritional requirements, number of remaining calories for ingestion, recent physical activity, and the food and/or beverages choices that are available for consumption.) Physical activity and dietary service program 200 determines meal recommendation 122 (e.g., food and beverages to consume by the individual) that are available for purchase based on menu information 166 that meet dietary plan 148. In the depicted embodiment, meal recommendations 122 reside on server 120. In another embodiment, meal recommendations 122 may reside on client device 110, fitness tracking device 140, smart appliance 180, and/or another computing device (not shown) provided, meal recommendation 122 is accessible by physical activity and dietary service program 200.

Retailer offer 124 are incentives (discounts, sales, promotions, specials, etc.), for products, goods, services, food, beverages, etc. that are offered by goods and service providers (e.g., vendor, restaurant, grocery store, virtual storefront, brick and mortar store, etc.) and/or proposition (i.e., act of offering or suggestion something to be considered, such as a proposed plan or an offer of terms for a transaction) as determined by physical activity and dietary service program 200. For example, retailer offer 124 is a discount for twenty percent off running shoes that are over one hundred dollars. In another example, retailer offer 124 is an offer for buyers of an organic smoothie to receive half off a subsequent purchase. In the above example, physical activity and dietary service program 200 determines retailer offer 124 based on a combination of one or more of the following: user information 116, dietary plan 118, physical activity data 119, user information 146, dietary plan 148, physical activity data 149, menu information 166, store inventory 172, and merchandise inventory 192. In the depicted embodiment, retailer offer 124 resides on server 120. In another embodiment, retailer offer 124 may reside on client device 110, fitness tracking device 140, restaurant device 160, grocery device 170, vendor device 190, and/or another computing device (not shown) provided, retailer offer 124 is accessible by physical activity and dietary service program 200.

Network 130 may be a local area network (LAN), a wide area network (WAN) such as the Internet, a wireless local area network (WLAN), any combination thereof, or any combination of connections and protocols that will support communications between client device 110, server 120, exercise machine 150, fitness tracking device 140, restaurant device 160, grocery device 170, smart appliance 180, vendor device 190, and other computing devices and servers (not shown), in accordance with embodiments of the inventions. Network 130 may include wired, wireless, or fiber optic connections.

Physical activity and dietary service program 200 is a program for tracking an individual's physical activity, calorie expenditure, and calorie consumption, etc. and providing meal recommendations 122 and retailer offer 124 based on user information 116, dietary plan 118, and/or physical activity data 119 and/or user information 146, dietary plan 148, and/or physical activity data 149 in real time. Physical activity and dietary service program 200 provides meal recommendation 122 based on shopping list 117, menu information 166, store inventory 172, and/or information from smart appliance 180 (e.g., information on food available that the individual owns that is present at a dwelling) that assist the user to make choices that coincide with dietary plan 118 or dietary plan 148 while also incorporating physical activity data 119 and/or physical activity data 149 (i.e., determines an appropriate food and/or beverage to consume based on nutritional content, type of physical activity, calories remaining for consumption, etc. to meet dietary goals, medical conditions, etc.). Physical activity and dietary service program 200 provides retailer offer 124 based on shopping list 117, menu information 166, store inventory 172, and/or merchandise inventory 192 that offer the individual incentives to purchase an item (e.g., food, beverage, product, service, merchandise, goods, etc.) that the individual utilizes to meet dietary plan 118 or dietary plan 148 and/or to perform physical activities as identified within physical activity data 119 and/or physical activity data 149.

Physical activity and dietary service program 200 sends and receives information to client device 110, fitness tracking device 140, exercise machine 150, restaurant device 160, grocery device 170, smart appliance 180, and/or vendor device 190 via physical activity and dietary service client program 114, physical activity and dietary service client program 144, physical activity and dietary service client program 154, physical activity and dietary service client program 164, physical activity and dietary service client program 174, physical activity and dietary service client program 184, and/or physical activity and dietary service client program 194. In the depicted embodiment, physical activity and dietary service program 200 resides on server 120. In another embodiment, physical activity and dietary service program 200 resides on client device 110, fitness tracking device 140, restaurant device 160, grocery device 170, smart appliance 180, vendor device 190, and other computing devices and servers (not shown), in accordance with embodiments of the inventions provided user information 116, dietary plan 118, physical activity data 119, user information 146, dietary plan 148, physical activity data 149, menu information 166, store inventory 172, smart appliance 180, and/or merchandise inventory 192 are accessible by physical activity and dietary service program 200.

Figure 2:
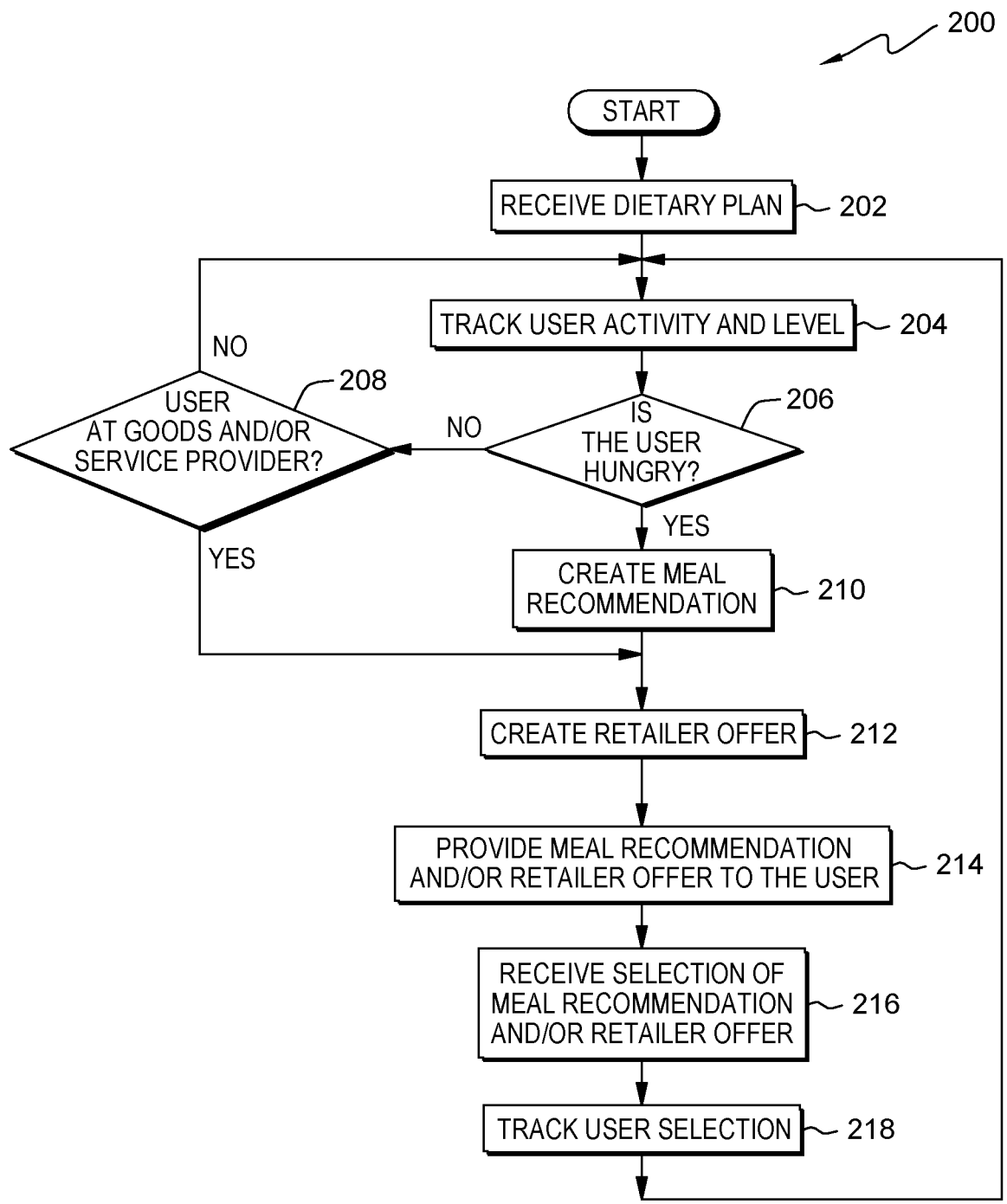
FIG. 2 is a flowchart depicting operational steps of an physical activity and dietary service program, on a server within the distributed data processing environment of FIG. 1, for tracking physical activity, calories expended, caloric intake and providing dietary and nutritional services and retailer incentives in real time, in accordance with an embodiment of the present invention.

FIG. 2 is a flowchart depicting operational steps of physical activity and dietary service program 200, a program for tracking physical activity, calories expended, caloric intake and providing dietary and nutritional services and retailer incentives in real time, in accordance with an embodiment of the present invention. In one embodiment, physical activity and dietary service program 200 initiates upon application of power (e.g., first time set up of fitness tracking device 140 and physical activity and dietary service client program 144, first time setup of physical activity and dietary service client program 114 on client device 110, etc.) In another embodiment, physical activity and dietary service program 200 is running as a background program that receives updates in real time from one or more of client device 110, fitness tracking device 140, exercise machine 150, restaurant device 160, grocery device 170, smart appliance 180, and vendor device 190 as an individual performs physical activity, consumes food and/or beverages, and/or as the individual interacts with a food and/or merchandise provider.

For example, the individual wakes up and begins to move and/or puts on fitness tracking device 140. Fitness tracking device 140 detects the change in the activity level and sends a notification to physical activity and dietary service program 200 to begin tracking (e.g., indicates an increase of physical activity that expends additional calories instead of a steady expenditure that maintains just necessary body functions). In some other embodiment, physical activity and dietary service program 200 initiates based upon detection of a request. In yet some other embodiment, physical activity and dietary service program 200 initiates upon detection of client device 110 and/or fitness tracking device 140. For example, the individual enters a store, and vendor device 190 detects and/or is notified of client device 110 and/or fitness tracking device 140 and initiates physical activity and dietary service program 200 to determine retailer offer 124.

In step 202, physical activity and dietary service program 200 receives dietary plan 118 or dietary plan 148 via physical activity and dietary service client program 114 or physical activity and dietary service client program 144 respectively. In one embodiment, physical activity and dietary service program 200 receives dietary plan 118 or dietary plan 148 as part of an initial set up (i.e., first time use). In another embodiment, physical activity and dietary service program 200 receives dietary plan 118 or dietary plan 148 as an update. In some embodiments, after initial setup, if an update is not made, physical activity and dietary service program 200 utilizes the instance of dietary plan 118 or dietary plan 148 utilized at set-up (e.g., stored version, initial settings, etc.). Dietary plan 118 or dietary plan 148 identifies a type of food plan a user intends to follow (e.g., vegan, paleo diet, ketogenic diet, gluten free, carbohydrate cycling), overall caloric intake, and the number of calories from each nutritional type (e.g., carbohydrate, fat, protein) for consumption that meet nutritional guidelines, physical goals (e.g., weight loss, weigh gain, maintenance, muscle building, lean muscle building, etc.) and/or medical conditions (e.g., blood glucose levels, lowering cholesterol, gastric bypass, etc.). Nutritional guidelines provide evidencebased food and beverage recommendations to promote health, prevent chronic disease, and assist individuals in reaching and maintaining a healthy weight. For example, nutritional guidelines indicate adult males between 19 and 50 should ingest 2,550 calories, where as a woman in the same age group should ingest 1,940 calories. For both men and women, carbohydrate intake should consist of approximately 45-65% of the caloric intake, fat (e.g., lipids, polyunsaturated and monounsaturated fats) should consist of 25-35% of the caloric intake, and protein intake should consist of 15-35% of caloric intake.

Additionally, physical activity and dietary service program 200 receives user information 116 or user information 146 (e.g., date of birth, gender, height, weight, cholesterol levels, blood pressure, a blood glucose profile, intensity level, and a type of athletic profile such as unspecified general fitness, triathlete, body builder, runner, swimmer, etc.) via physical activity and dietary service client program 114 or physical activity and dietary service client program 144 respectively. In one embodiment, physical activity and dietary service program 200 creates dietary plan 118 based on user information 116 and/or user information 146. For example, an individual identifies athlete type as a body builder; therefore, physical activity and dietary service program 200 creates dietary plan 118 to increase muscle mass and reduce body fat, while maintaining proper nutrition based on nutritional guidelines for the height, weight, and gender of the individual. In another embodiment, physical activity and dietary service program 200 creates dietary plan 118 or dietary plan 148 based on goals as set by weight goals (e.g., weight loss, maintenance, gain). In some other embodiments, physical activity and dietary service program 200 creates dietary plan 118 and dietary plan 148 based on a type of diet (e.g., vegetarian, vegan, paleo diet, ketogenic diet, gluten free diet, vegan, carbohydrate cycling, Mediterranean, etc.). In yet another embodiment, physical activity and dietary service program 200 creates dietary plan 118 and dietary plan 148 are based on and/or medical conditions (e.g., allergies, diabetes, high blood pressure, injuries, vitamin/nutritional deficiencies, pregnancy, illness, etc.). In yet some other embodiment, physical activity and dietary service program 200 creates dietary plan 118 and dietary plan 148 based on one or more of the aforementioned embodiments.

In some embodiments, physical activity and dietary service program 200 also receives a basal metabolic rate (BMR) as part of user information 116 or user information 146 (e.g., personal knowledge, dietician calculated BMR, software calculation based on measurements, etc.). BMR is the amount of calories an individual requires to perform daily life sustaining functions (i.e., the rate of your metabolism or the amount of calories an individual burns at rest) and the number of calories burned. In another embodiment, physical activity and dietary service program 200 calculates the BMR based on user information 116 or user information 146. For example basal metabolic rate is calculated as:

BMR of a Woman=(4.7*Height)+(4.35*Weight)−(4.7*Age)+655

BMR of a Man=(12.7*Height)+(6.23*Weight)−(6.8*Age)+66

To refine the BMR (e.g. calculate a total energy expenditure), in some embodiments, physical activity and dietary service program 200 multiples the BMR value by an intensity level (i.e., sedentary, lightly active, moderately active, very active, and extra active). For example sedentary (i.e., little to no exercise) is 1.2, lightly active (i.e., exercising 1-to-3 days each week) is 1.375, moderately active (i.e., exercising moderately 3-to-5 days) is 1.55, very active (i.e., hard exercise 6-to-7 days a week) is 1.725, and extra active (i.e., very physically challenging jobs or exercise, such as 2-a-day workouts) is 1.9.

In one embodiment, physical activity and dietary service program 200 receives caloric intake values based on dietary plan 118 or dietary plan 148 that was designed for the individual (e.g., created nutritional plan by a dietician for entry or upload for utilization). In another embodiment, physical activity and dietary service program 200 calculates caloric intake values based on the BMR, nutritional guidelines, physical goals, intensity level (e.g., activity level) and/or medical conditions. In some embodiments physical activity and dietary service program 200 adjusts the percentages of each food type (e.g., carbohydrates, fats, proteins, etc.) to meet physical goals and the athlete type. For example, a body builder would ingest additional protein to assist in building muscle mass than a person losing weight.

For example, a user of fitness tracking device 140 follows prompts from physical activity and dietary service client program 144 to enter user information 146 with respect to: date of birth, gender, height, weight, cholesterol levels, blood pressure, a blood glucose profile, and a type of athletic profile (e.g., unspecified general fitness, triathlete, body builder, runner, swimmer, etc.). Physical activity and dietary service program 200 calculates a BMR based on user information 146. Physical activity and dietary service program 200 adjusts BMR value and/or caloric intake targets to meet the physical goals (e.g., decreases caloric intake by 500 calories a day to reduce weight, increases caloric intake by 500 calories to gain weight, increases calorie intake on a cheat day, etc.) without depriving the individual of proper nutrition (e.g., avoids drastic cuts of calorie intake that causes the individual to enter starvation mode and slow the metabolism). Additionally, physical activity and dietary service program 200 prompts the user to enter dietary plan 148 manually, upload dietary plan 148, and/or to enter dietary plan 148 through a selection of predefined options via physical activity and dietary service client program 144. Physical activity and dietary service program 200 calculates number of calories allowed from each food type (e.g., carbohydrates, fats, proteins, etc.) as defined by dietary plan 118 or dietary plan 148 to match nutritional guidelines with the calculated caloric intake to meet physical and/or medical goals. For example physical activity and dietary service program 200 determines a vegetarian will eat a combination of nuts, seeds, and beans to receive protein, Conversely, physical activity and dietary service program 200 determines an individual with high cholesterol that is an omnivore (i.e., eats both plants and animals) will eat either fish or poultry to receive protein.

In step 204, physical activity and dietary service program 200 tracks user activity (e.g., physical activity data 119, physical activity data 149, and/or physical activity data 159) and an exercise intensity level. Exercise intensity refers to how much energy is expended when exercising (i.e., a physiological measurement that expresses an energy cost of physical activities, defined as a ratio of a metabolic rate during a specific physical activity to a reference metabolic rate), and varies with each individual. Exercise intensity includes at least three categorized levels of low (e.g., sleeping, walking under 3.0 miles per hour, and sitting), moderate (e.g., walking above 3.0 miles per hour bicycling and calisthenics), and vigorous (e.g., jogging, running, bicycling over 10 miles per hour). The exercise intensity and heart rate of the individual effects the order of fuel recruitment (i.e., determines whether the calories expended come from carbohydrates, fat, or protein) that a body utilizes and adaptations the body makes after exercise. For example, low intensity, lower heart rate (e.g., intensity of 65-75% of maximum heart rate range results in fat burning), and long duration exercise provides a larger percentage of fat calories burned as the body does not need to quickly and efficiently produce energy versus a high intensity activity and a higher heart rate (e.g., intensity of 75-100% of maximum heart rate range results in carbohydrate burning) expends a larger percentage of carbohydrates calories as carbohydrates quickly produce energy.

In one embodiment, without a heart rate monitor, physical activity and dietary service program 200 calculates the calories burned as:

Calories=Intensity*Weight*Duration

For example, an individual goes for a 45 minute jog but does not wear fitness tracking device 140. Through user interface 112 and physical activity and dietary service client program 114, the individual manually enters an exercise activity with a duration, a perceived intensity level and/or an activity level associated with the physical activity (e.g., running is classified as vigorous activity). Physical activity and dietary service client program 114 utilizes the entered information with user information 116 to calculate the number of calories burned, however, the calories burned are an approximation due to the lack of actual monitored data.

In another embodiment, physical activity and dietary service program 200 receives user activity and the exercise intensity level through physical activity and dietary service client programs 114, 144, and 154 without heart rate data. Physical activity and dietary service client programs 114, 144, and/or 154 calculate physical activity data 119, 149, and/or 159, based on available information and software that calculates calorie expenditure. For example, exercise machine 150 does not include heart rate monitor sensors in the hand grips, or a user does not make contact with the heart rate monitor sensors that allow heart rate monitoring. Therefore, physical activity and dietary service client program 154 calculates the calories expended based on user information 156, the routine selected, resistance levels, speed, and duration of the exercise performed and sends physical activity data 119 to physical activity and dietary service program 200. However, the calories expended as calculated by physical activity and dietary service client program 154 may include an error due to the lack of heart rate data, but are more accurate than the aforementioned embodiment that bases the calories expended on a perceived intensity, as exercise machine 150 includes actual data that translates to an intensity level (e.g., resistance, speed, and routine selected by the individual).

In some other embodiment in which heart rate monitoring data is available, physical activity and dietary service client programs 114, 144 and/or 154 calculate physical activity data 119, physical activity data 149, and/or physical activity data 159 with the calories burned based on the relationship between heart rate (HR) and oxygen uptake (VO2), user information 116 and physical activity data 119, user information 146 and physical activity data 149 and/or user information 156 and physical activity data 159. During steady-state cardiovascular exercise, a relatively fixed relationship exists between HR and VO2. VO2 max refers to the maximum volume of oxygen the individual can use during exercise. An increase in workload requires an increase in VO2 which leads to an increase in HR and conversely a decrease in VO2 leads to a decrease in HR. In one embodiment, physical activity and dietary service client program 114, 144, and or 154 obtains an individual's HRmax (e.g., heart rate while exercising), HRrest (e.g., resting heart rate as taken when an individual wakes up in the morning), and VO2max, from user information 116, user information 146, and/or user information 156 that a user enters, as measured through performance of a fitness test with fitness tracking device 140, and/or estimates based on user information 116, 146, and/or 156 (i.e. age and gender with heart rate guidelines). Physical activity and dietary service client program 114, 144, and or 154 establishes a "scale" for the individual based on HRmax, HRrest and VO2max and the fixed relationship. Physical activity and dietary service client programs 114, 144, and/or 154 calculates an exercise workload with respect to the scale, which incurs variation with the monitoring of the HR in real time (i.e., heart rate is updated and provided through heart rate monitoring functions of fitness tracking device 140 and/or exercise machine 150). Physical activity and dietary service client programs 114, 144, and 154 calculate calories expended as a product of the calculated exercise workload and the weight of the individual as entered within user information 116, 146, and/or 159. Physical activity and dietary service client program 114, 144, and or 154 send physical activity data 119, physical activity data 149, and/or physical activity data 159 to physical activity and dietary service program 200 for utilization.

In yet another embodiment, physical activity and dietary service program 200 tracks and calculates calories burned based on received physical activity data 119, physical activity data 149, and/or physical activity data 159 in a similar manner as explained in the aforementioned embodiments. For example, exercise machine 150 via physical activity and dietary service client program 154 sends physical activity data 159 to physical activity and dietary service program 200 with user information 156. Physical activity and dietary service program 200 utilized the received information to calculate the calories burned. In some embodiment, physical activity and dietary service program 200 replaces default values (e.g., user does not enter a weight, age, gender, etc.) and calculates an updated calorie expenditure based on actual data instead of defaults. While tracking physically activity is shown as a single step 204, physical activity and dietary service program 200 tracks user activity throughout the steps of physical activity and dietary service program 200. For example, fitness tracking device 140 is a wearable device which records physical activity as long as fitness tracking device 140 maintains power and is worn by an individual. Additionally, in some embodiments, physical activity and dietary service program 200 estimates calories expended based on the BMR if physical activity and dietary service program 200 does not receive physical activity data 119, physical activity data 149, and/or physical activity data 159. For example, the user removes fitness tracking device 140 at 10 p.m. and begins wearing the device at 6 a.m. Physical activity and dietary service program 200 determines the user is sleeping and calculates an estimated number of calories associated with sleeping utilizing user information 146.

In decision 206, physical activity and dietary service program 200 determines whether the user is hungry. In one embodiment, physical activity and dietary service program 200 receives an input form the user to enter and/or select a meal or snack, which physical activity and dietary service program 200 utilizes to determine the user is hungry. In another embodiment, physical activity and dietary service program 200 determines that a user is hungry based on standard meal times (e.g., breakfast eaten between 6 a.m. and 8 a.m., lunch eaten between 11:30 a.m. and 1 p.m., dinner eaten between 5 p.m. and 6:30 p.m.). In some other embodiments, physical activity and dietary service program 200 determines that a user is hungry based on a time between an event (e.g., within an hour of waking, optimal time between meals, optimal time for a snack between meals, three hours prior to bedtime, within a specified time after a workout, blood sugar profile, etc.). For example, physical activity and dietary service program 200 identifies a dip in the blood sugar of the individual around 2 p.m. based on the blood glucose profile. Physical activity and dietary service program 200 determines that while the individual may not feel hungry, a snack should be recommended and/or consumed by the individual to help raise the blood sugar level of the individual and therefore, physical activity and dietary service program 200 determines the user is hungry.

In yet another embodiment, physical activity and dietary service program 200 determines whether the user is hungry based on prior meal and snack times (e.g. previously recorded meal and snack times that physical activity and dietary service program 200 stored as history data). For example an individual eats breakfast at 8 a.m. every day, lunch at 12:05 p.m., a snack at 3:30 p.m., and dinner at 6 p.m. The local time for the user on fitness tracking device 140, client device, or server 120 is 8:10 a.m. Physical activity and dietary service program 200 determines the user is therefore hungry based on the history data and the current local time. Additionally, physical activity and dietary service program 200 may determine the user is hungry if the user has not identified an eating activity within a certain period of time within which the user normally eats (i.e., determines the user has not eaten a meal within a time frame based on history and/or standard meal times). Continuing the example, the local time is 1 p.m., and the user did not enter consumption of breakfast, a snack and/or lunch. Physical activity and dietary service program 200 determines the user skipped breakfast and is hungry based on the lack of a consumption entry.

In yet some other embodiment, physical activity and dietary service program 200 determines that a user is hungry based on location. For example, the GPS location for fitness tracking device 140 or client device 110, identifies the user is at a restaurant. In another example, fitness tracking device 140 or client device 110 connects to a local network of the restaurant that "checks in" the individual as being at the restaurant, etc. Physical activity and dietary service program 200 receives the check in notification at the restaurant and determines the user is hungry. In another embodiment, physical activity and dietary service program 200 receives a notification from smart appliance 180, and physical activity and dietary service program 200 determines the user is hungry. For example smart appliance 180 is a refrigerator, and smart appliance 180 detects that the user opens the door. Physical activity and dietary service program 200 receives the notification from smart appliance 180 and determines the user is hungry. In another example, the user accesses the Internet via smart appliance 180 and requests a dinner recipe based on the food contents of smart appliance 180. Physical activity and dietary service program 200 receives the request for a dinner recipe and determines that the user is hungry. Additionally, in some embodiments, physical activity and dietary service program 200 delivers a prompt to the user based on one or more of aforementioned embodiments and inquires whether the user is hungry. Physical activity and dietary service program 200 determines whether the user is hungry based on the received response to the inquiry.

Conversely, in decision 206, physical activity and dietary service program 200 determines a user is not hungry based on the negative of the aforementioned embodiments (e.g., time does not match a standard eating time, time between eating events it less than the defined time, time does not match history time, user location is not at a restaurant, user enters no to the prompt, etc.). For example, the individual ate a late brunch at 10:30 a.m., therefore physical activity and dietary service program 200 determines the user is not hungry at 11:30 a.m. when the individual eats lunch based on the historical data as a less than an hour has passes between an actual eating event and a historical eating event, and the defined time between breakfast and lunch eating events is set at 3.5 hours.

If physical activity and dietary service program 200 determines the user is hungry (decision 206, yes branch), then physical activity and dietary service program 200 creates meal recommendation 122 (step 210). If physical activity and dietary service program 200 determines the user is not hungry (decision 206, no branch), then physical activity and dietary service program 200 determines whether the user is at a goods and/or service provider (decision 208).

In decision 208, physical activity and dietary service program 200 determines whether the user is at a goods and/or service provider. In one embodiment, physical activity and dietary service program 200 determines that the user is at a goods and/or service provider based on location. For example, the GPS location for fitness tracking device 140 or client device 110, identifies the user is at a mall. Conversely, physical activity and dietary service program 200 determines that the user is not at a goods and/or service provider based on location. For example, the GPS location of the user is at the home of the individual, a library, a highway, and/or another location not related to good and/or service, and therefore, physical activity and dietary service program 200 determines that the user is not at a goods and/or service provider based on the location not matching a retailer location. In another embodiment, physical activity and dietary service program 200 receives a check in notification from client device 110, fitness tracking device 140, grocery store device, and/or vendor device 190 via physical activity and dietary service client program 114, 144, 174, and/or 194. For example, client device 110 and/or fitness tracking device 140 connects to a local network of a goods and/or service provider that "checks in" the individual (e.g., identifies the location of the individual to be at a specific store), etc. Physical activity and dietary service program 200 determines the user is at a goods and/or service provider based on the check in information. In some other embodiment, physical activity and dietary service program 200 connects to an indoor positioning location system (not shown) and receives location data from the indoor positioning system. In yet another embodiment, physical activity and dietary service program 200 receives a location and/or a store name from the user. For example, a user of client device 110, enters a store name and location for a horse riding stable to check for available instances of retailer offers 124 from the horse riding stable.

Additionally, in some embodiments, physical activity and dietary service program 200 identifies a specific store and/or group of stores associated with the location. For example, the individual enters a shoe store. Physical activity and dietary service program 200 identifies the shoe store by geographic location and/or through check in information. In another example, physical activity and dietary service program 200 identifies a location associated with a mall. Physical activity and dietary service program 200 identifies all of the stores that provide goods and services within the mall for further utilization. In another embodiment, physical activity and dietary service program 200 connects to an indoor positioning location system (not shown). Physical activity and dietary service program 200 receives a specific store based on the location of the individual as identified by the indoor positioning system. In some other embodiment, physical activity and dietary service program 200 utilizes one or more of the aforementioned embodiments to identify a location and/or a specific store. In yet some other embodiment, physical activity and dietary service program 200 determines the individual is at home, however the individual is shopping through online stores (e.g., tracks Internet activity, searches, etc., through web browser activity on client device 110). Physical activity and dietary service program 200 identifies the store through which the online shopping is taking place through data mining of a web browser, Internet activity, and/or web browser history for further utilization to create retailer offers 124 for online stores.

If physical activity and dietary service program 200 determines the user is at a goods and/or service provider (decision 208, yes branch), then physical activity and dietary service program 200 creates retailer offer 124 (step 212). If physical activity and dietary service program 200 determines the user is not at a goods and/or service provider (decision 208, no branch), then physical activity and dietary service program 200 tracks user activity (step 204).

In step 210, physical activity and dietary service program 200 creates meal recommendation 122. Physical activity and dietary service program 200 identifies the number of calories for consumption and/or nutritional requirements. In one embodiment, physical activity and dietary service program 200 calculates the number of calories for consumption based on a combination of user information 116, dietary plan 118, and/or physical activity data 119. For example, physical activity and dietary service program 200 calculates an individual's BMR based on user information 116. Physical activity and dietary service program 200 combines the calculated BMR with the calculated number of expended calories as identified within physical activity data 119, in order to determine an overall number of calories to consume. In one embodiment, physical activity and dietary service program 200 utilizes the overall number of calories to consume without changes (e.g., maintains current weight). In another embodiment, physical activity and dietary service program 200 adds or subtracts a specified number of calories to or from the calculated number of overall calories to consume to create an adjusted number of overall calories to consume that meets the physical goals of dietary plan 118. For example, the individual sets a goal to lose weight, therefore, physical activity and dietary service program 200 subtracts 500 calories from the overall number of calories for consume to promote weight loss. Physical activity and dietary service program 200 stores the calculated and/or adjusted caloric consumption value to utilize for consumption tracking and to create meal recommendation 122.

In another embodiment, physical activity and dietary service program 200 retrieves a total number of calories allowed for consumption from dietary plan 118 or dietary plan 148. For example, the individual is under the guidance of a medical professional or personal trainer, in which a specific instance of dietary plan 148 was created. Dietary plan 148 identifies a total number of calories to consume, a total number of calories allowed for consumption that are associated with a specific meal type (e.g., breakfast, lunch, dinner, snack, etc.), a time frame in which the calories should be consumed, and/or the type of fuel (e.g. nutritional content and type of food such as carbohydrate, fat, or protein) that an individual should consume.

In some other embodiments, physical activity and dietary service program 200 retrieves a remaining number of calculated allowed calories for consumption. For example, throughout a specified time period, physical activity and dietary service program 200 updates the number of calories that remain to be consumed as described in greater detail in step 220 (e.g., decreases the remaining number of calories to consume by the number of calories ingested). Additionally, physical activity and dietary service program 200 varies (e.g., increases or decreases) the number of calories allowed for consumption (e.g., calculated overall number of calories, adjusted overall number of calories, and/or remaining number of calories) based on physical activity data 119, 149, or 159 and consumption information associated with meal recommendation 122.

For example, initially when an individual first wakes up, physical activity and dietary service program 200 sets the number of calories to consume to match the number of calories that the individual expends in a day based on BMR with an adjustment based on dietary plan 118 (e.g., calculated overall number of calories, adjusted overall number of calories). As the day progress, the individual performs physical activity data 119, which may cause physical activity and dietary service program 200 to increase the number of calories that the individual may consume depending on dietary plan 118. However as the individual consumes food (e.g., a meal, a snack, a beverage, etc.), physical activity and dietary service program 200 subtracts the calories associated with the consumed food from the calculated overall number of calories or the adjusted overall number of calories for consumption to create the remaining allowed number of calories for consumption (i.e., created the first time a user consumes food within the specified time period).

Additionally, in subsequent iterations, physical activity and dietary service program 200 adjusts the remaining allowed number of calories for consumption with meal information and/or physical activity data 119 until the end of the specified time period (e.g., user goes to bed and begins a new day, calories allowed within a time period of for a meal, time period associated with between meals, etc.).

In yet some other embodiment, physical activity and dietary service program 200 creates meal recommendation 122 based on physical activity data 119 or physical activity data 149. For example, based on physical activity data 149, physical activity and dietary service program 200 identifies the individual just finished a 60 mile bicycle ride. Physical activity and dietary service program 200 determines that leg cramps may occur due to the vigorous, prolonged activity (e.g., repetitious motion over a long period of time) and from maintaining the same position for a prolonged (e.g., lengthy) amount of time, dehydration, low magnesium levels, and low potassium levels. Additionally, physical activity and dietary service program 200 determines the individual is hungry, as the individual should consume at least a beverage to replenish nutrients and to rehydrate based on the distance, intensity level, and/or duration of the bicycle ride as identified within physical activity data 149. Physical activity and dietary service program 200 determines meal recommendation 122 that includes food items and beverages to increase magnesium levels (e.g., suggests nuts, seeds, spinach, and bananas), increase potassium levels (e.g., bananas, yogurt, apples, spinach, etc.) and to assist in maintaining hydrations and/or to recover from dehydration (e.g., water, sports recovery drink, etc.)

In one embodiment, physical activity and dietary service program 200 determines the individual is at a restaurant. Physical activity and dietary service program 200 retrieves menu information 166. Menu information 166 includes the caloric value and nutritional content associated with individual food selections that an individual is able to order off of a predefined menu, which are prepared and/or served at a restaurant and/or food service provider. Physical activity and dietary service program 200 compares the meals (e.g., possible food selections) included within menu information 166 to the calculated overall number of calories, adjusted overall number of calories, or remaining allowed number of calories for consumption. Based on the comparison physical activity and dietary service program 200 identifies available meal options within menu information 166 that do not exceed the number of remaining allowed number of calories for consumption and/or are within a tolerance (e.g., does not exceed more than 10% of the remaining allowed number of calories, etc.) Additionally, physical activity and dietary service program 200 analyzes the available meal options with respect to dietary plan 118 and/or remaining types of fuel for consumption. Based on the analysis of the available meal options with respect to dietary plan 118, physical activity and dietary service program 200 identifies available meal options within menu information 166 that meet nutritional requirements and/or are within a tolerance (e.g., within plus or minus 5% of each fuel type, remains within the percentage intake of carbohydrates, fat, and protein depending on gender, etc.). Physical activity and dietary service program 200 combines the results of the comparison and the analysis to identify meal recommendations 122 that meet both allowed calorie consumption and nutritional content (i.e., identifies meals for menu information 166 that are included in both the calorie analysis and nutritional analysis). In some embodiments, physical activity and dietary service program 200 may provide meal recommendation 122 with a recommended portion size (e.g., small or medium instead of large, half size portion, etc.) to allow a greater selection from menu information 166, while still maintaining dietary plan 118 and the remaining number of allowed calories for consumption. In some other embodiment, physical activity and dietary service program 200 ranks meal recommendations 122 in an order that maintains dietary plan 118 the remaining number of allowed calories for consumption (e.g., identifies an order of preference, in which the order of preference ranks the highest matching instance of meal recommendation 122 with dietary plan 118 and the remaining number of allowed calories for consumption to the lowest matching instance of meal recommendation 122).

For example, the individual is on a carbohydrate cycling diet (i.e., alternate carbohydrate intake on a daily, weekly, or monthly basis in order to lose fat, maintain physical performance while dieting, or overcome a weight loss plateau). A weekly carbohydrate cycling diet include two high-carbohydrate days, two moderate-carbohydrate days and three low-carbohydrate days, with a similar protein intake for each day, and fats vary with the carbohydrates (i.e., high-carbohydrate day equals low-fat intake, whereas the low-carbohydrate days equals high-fat intake). The individual is at an Italian restaurant for dinner on a high carbohydrate day and has 700 calories remaining that may be consumed, and according to dietary plan 118 the day is a high-carbohydrate intake day. Physical activity and dietary service program 200 identifies: a chicken piccatta at 350 calories, a lasagna at 640 calories, and a spaghetti dinner at 640 calories from menu information 166 as being within the allowed number of remaining calories. Physical activity and dietary service program 200 identifies the nutritional content of the chicken piccatta to be 21 g of fat, 11 g of carbohydrates, and 33 g of protein; the lasagna dinner to be 36 g of fat, 39 g of carbohydrates, and 40 g of protein; and the spaghetti with meat sauce to be 22 g of fat, 85 g of carbohydrates, and 26 g of protein. Physical activity and dietary service program 200 identifies the spaghetti with meat sauce as meal recommendation 122 based on the high number of carbohydrates and the lower fat content. As an added option, physical activity and dietary service program 200 adds a half portion of eggplant parmigiana at 530 calories, 27 g of fat, 57 g of carbohydrates, and 15 g of protein (i.e., full portion is double the values identified) as the second ranked item, the chicken piccatta as the third item, and the lasagna as the fourth item.

In an alternate embodiment, physical activity and dietary service program 200 creates meal recommendation 122 based on purchase trends for multiple individuals. For example, for a month, every Thursday, fifty percent of the patrons of the restaurant purchase a low carbohydrate meal and physical activity data 119 for the individuals indicates the patrons completed at least a five mile run. Physical activity and dietary service program 200, utilizes the data to create and/or recommend new low carbohydrate specials each Thursday and/or to provide special pricing (e.g., retailer offers 124) to entice the individuals to return.

In another embodiment, physical activity and dietary service program 200 determines the individual is at home (e.g., receives notification from smart appliance 180 that coincides with dinner time.) Physical activity and dietary service program 200 identifies an inventory of the food items that the user has available within smart appliance 180 (e.g., identifies the food contents of the refrigerator). Physical activity and dietary service program 200 retrieves calorie content (e.g., caloric value) and nutritional information (e.g., nutritional content) associated with the inventory of food items (e.g., retrieves standard calorie and nutrition information from a database of food items). In one embodiment, physical activity and dietary service program 200 identifies recipes available through Internet recipe cites and/or dietary meal planning services (e.g., cites which provide nutritionally balanced meals that may also incorporates specific dietary plans) based on the contents of smart appliance 180. Physical activity and dietary service program 200 provides recipes to the individual to prepare a meal and/or snack based on the contents of the smart appliance 180 that meet the remaining number of allowed calories for consumption and dietary plan 118. The recipes include serving sizes (i.e., gauges the amount of food in a single serving to assist in portion size and control), calories per serving, and/or nutritional content for further utilization to track consumption. For example, physical activity and dietary service program 200 provides a recipe to the individual, in which the caloric value and nutritional content of a serving size of the recipe meets the remaining allowed calorie consumption and nutritional content requirements. In another embodiment, physical activity and dietary service program 200 provides a list of the food items that meet the remaining number of allowed calories for consumption and dietary plan 118 for the individual to select from. In some other embodiment physical activity and dietary service program 200 also provides an indication of what purpose the food item serves (e.g., meal type), calories, and nutritional content. For example physical activity and dietary service program 200 classifies and apple with 72 calories and 19 g of carbohydrates as a snack and raw chicken when prepared as a meal with 142 calories in a half a skinless chicken breast, 0 g of carbohydrates, 27 g of protein, and 3 g of fat.

In step 212, physical activity and dietary service program 200 creates retailer offer 124. Physical activity and dietary service program 200 determines the type of business (e.g. shoe store, clothing store, exercise equipment, gym, spa, restaurant, nutrition store, grocery store, etc.), which the individual is patronizing (i.e., frequenting as a customer, store the individual is shopping at, etc.). In one embodiment, physical activity and dietary service program 200 accesses user information 116 or 146, physical activity data 119 or 149, dietary plan 118 or 148, and/or shopping list 117 to identify a type of product and/or service that the individual may be interesting in purchasing to create retailer offer 124. For example shopping list 117 specifies an exact item and/or type the individual plans to buy (e.g., 16 oz jar peanut butter). In another embodiment, physical activity and dietary service program 200 accesses store inventory 172 and/or merchandise inventory 192 to identify items that are in stock that may interest the user and/or match the identified type of product and/or service to create retailer offer 124. In some other embodiment, physical activity and dietary service program 200 checks a number of items in inventory (e.g., in stock), the wholesale price, and/or a length of time that items within store inventory 172 and/or merchandise inventory 192 have been in stock to create retailer offer 124. In yet another embodiment, physical activity and dietary service program 200 identifies the location of the individual within a business based on an indoor positioning system and monitors the amount of time the user remains in an area in order to create retailer offer 124.

In an alternate embodiment, physical activity and dietary service program 200 access prior shopping history associated with the individual. For example, the individual frequents the nature food store each week. Physical activity and dietary service program 200 maintains a record of the businesses that the individual frequents and/or makes purchases from. If physical activity and dietary service program 200 determines the individual has visited and/or made purchases from the business previously, physical activity and dietary service program 200 reviews the record to identify repeat purchases and/or for the types of purchases made at the store to create retailer offer 124. In some embodiments, physical activity and dietary service program 200 determines retailer offer 124 through one or more of the aforementioned embodiments to create retailer offer 124 (i.e., as physical activity and dietary service program 200 utilizes more data utilized to create retailer offer 124, physical activity and dietary service program 200 increases the likelihood of creating retailer offer 124 that will result in a sale, as the information eliminates options and provides a more specific instance of retailer offer 124 to the individual). Physical activity and dietary service program 200 creates retailer offer 124 with a unique identifier (e.g., promotional code, bar code, reference number, etc.) that identifies each individual for tracking upon redemption.

For example, the user is at a sports store that sells sports related equipment and accessories. Based on user information 116 and or physical activity data 119, physical activity and dietary service program 200 identifies the individual is a runner. Physical activity and dietary service program 200 determines the user may be interested in purchasing running clothing, running shoes, and/or a treadmill. Based on prior shopping history, physical activity and dietary service program 200 identifies the user bought a treadmill a month prior, therefore physical activity and dietary service program 200 removes the treadmill options from the items for purchase and maintains running clothing and running shoes as purchase options. Through an indoor positioning system, physical activity and dietary service program 200 determines the user is located in women's clothing and remains within the department. Physical activity and dietary service program 200 accesses merchandise inventory 192 and identifies a surplus of two brands of s running clothing. Therefore, physical activity and dietary service program 200 reviews the wholesale price and the length of time in inventory for the surplus items and calculates retailer offer 124 specific to the surplus clothing brand items. Additionally in some embodiments physical activity and dietary service program 200 creates a lesser retailer offer 124 for the clothing brands that are not a surplus and or for running shoes to try to encourage the individual to make one or more purchases.

In yet some other embodiment, physical activity and dietary service program 200 creates retailer offer 124 based on physical activity data 119 or physical activity data 149 in real time and/or within a defined period of time in which the physical activity (e.g., a workout) occurs and an arrival time of the individual at a retailer store. (e.g., surrounds a workout, immediately following a workout, within an hour of completing a workout, a number of hours prior to a workout, time frame defined by the individual based on personal preferences, a time as defined within dietary plan 118 in conjunction with the occurrence of a workout, etc.). The defined period of time is a predefined time that surrounds a workout (e.g., up to an hour before a workout and within a half hour of completing a workout), a maximum elapsed time, a minimum time prior to, following, or relative to a workout (e.g., physical activity), in which the user transitions from a physical activity and arrives at a location to consume food items and/or to make a purchase of an item, or the converse (e.g., makes a purchase prior to a workout). For example, an individual swims each day at 1 pm. Physical activity and dietary service program 200 includes a defined time period that states the individual should not consume food items up to one hour prior to the swimming activity, therefore the latest the user should finish consuming a meal or snack is at 12 pm. After the hour swimming activity, physical activity and dietary service program 200 includes a defined time that states the individual should consume food items within an hour of completion of the swim activity to rehydrate and replenish nutrients. Physical activity and dietary service program 200 calculates an elapsed time between completion of the physical activity and the individual's arrival time at the store (i.e., tracks the actual time the physical activity ended and the actual arrival time of the individual at the store, and calculates the time difference as the elapsed time). Physical activity and dietary service program 200 determines whether the elapsed time is within the defined period of time (i.e., period of time that surrounds and/or encompasses the time of the workout). If physical activity and dietary service program 200 determines the elapsed time is within the defined period of time, then physical activity and dietary service program 200 recreates the retailer offer 124 based on the elapsed time (e.g., favors or increase an importance of the physical activity that occurs while recreating retailer offer 124). In other words, physical activity and dietary service program 200 creates retailer offer 124 as a physical activity based proposition, which is based on an anticipated physical activity (e.g., a specified time prior to the occurrence of a workout) and/or after the actual occurrence of a workout (e.g., a specified time after the occurrence of a workout, but before a maximum time passes). If physical activity and dietary service program 200 determines the elapsed time is not within the defined period of time, then physical activity and dietary service program 200 provides retailer offer 124 without changes, and or appends retailer offer 124 with additional instances of retailer offer 124.

Continuing the example pertaining to the 60 mile bicycle ride, physical activity and dietary service program 200 determines the individual is at an organic smoothie store. Due to the potential for leg cramps and to the nutrients expended with the physical exercise, physical activity and dietary service program 200 determines the individual is hungry (e.g., should consume a food and/or beverage that aids in dehydration, and raising magnesium and low potassium levels). Physical activity and dietary service program 200 calculates an elapsed time between completion of the bicycle ride and the individual's arrival time at the store. As the individual ended the bicycle ride at the organic smoothie store the elapsed time is minimal (e.g., within minutes of completion of the bicycle ride, less than an hour of completing the workout, within the defined period of time). Physical activity and dietary service program 200 determines meal recommendation 122 as the banana, strawberry smoothie, which includes apple juice, yogurt, and spinach in the ingredients in addition to the strawberries and bananas, which will assist in replenishing the depleted nutrients and assist in the restoration of hydration. To encourage the user to purchase the strawberry banana smoothie, physical activity and dietary service program 200 created retailer offer 124 for three dollars off the price of the strawberry banana smoothie and/or a free upgrade in size for the strawberry banana smoothie. If physical activity and dietary service program 200 determines the user is at a retail store (e.g., grocery store, convenience store, pharmacy, gas station, etc.) instead of a restaurant (i.e., an establishment that sells prepared foods and/or beverages from a menu), then physical activity and dietary service program 200 creates retailer offer 124 for a discount on a sports drink.

In step 214, physical activity and dietary service program 200 provides meal recommendation 122 and/or retailer offer 124 to the individual (e.g., provides a proposition to the individual which suggests meal recommendation 122 to be considered for purchase for consumption and/or to provide retailer offer 124 offer that identifies terms for a transaction that includes special pricing (e.g., sales, discounts, etc.) for meal recommendation 122 and/or the purchase of goods and/or services). In one embodiment, physical activity and dietary service program 200 updates a display of restaurant device 160 to provide meal recommendation 122 and/or retailer offer 124. For example at a drive through window, a user views a placed order on a drive thru order confirmation box. Prior to ordering, physical activity and dietary service program 200 changes the display of the drive thru order confirmation box to display meal recommendation 122 and/or retailer offer 124. In another example, restaurant device 160 is a table top computing device (e.g., virtual server). Physical activity and dietary service program 200 updates the display to include a personalized tab that displays meal recommendation 122 and/or retailer offer 124 automatically and/or for selection by the individual for viewing. In another embodiment, physical activity and dietary service program 200 sends meal recommendation 122 and/or retailer offer 124 for display on user interface 112 and/or user interface 142. In some other embodiment, physical activity and dietary service program 200 sends user interface 162 meal recommendation 122 and/or retailer offer 124 to an instance of vendor device 190 associated with a sales associated or an instance of restaurant device 160 associated with a server that the sales associate or server views and then utilizes as the bases of a discussion with the customer that enhances the interaction with a personal experience through a human interface that delivers the recommendations. For example, the server is notified of the patron's goal to lower cholesterol, and therefore, the server recommends a broiled salmon special instead of fettuccini alfredo from the menu. In yet another embodiment, physical activity and dietary service program 200 displays meal recommendation 122 on user interface 182 of smart appliance 180 as a recipe, description of a meal, and/or as available food items for viewing by the individual.

In step 216, physical activity and dietary service program 200 receives a selection of meal recommendation 122 and/or retailer offer 124 via user interface 112, 142, or 182 from the individual (e.g., user enters information directly), via user interface 162 (e.g., entered by the individual and/or a second party such as a server or sales associate), from a receipt (e.g., scans a bar code, inputs a transaction number, inputs a promotional code, etc.) and/or by scanning a Quick Response Code (QR code). A QR code is a type of matrix barcode (i.e., two-dimensional barcode) that contains information about the item (e.g., product, purchase, food item, consumable good, service, etc.) to which it is attached that uses four standardized encoding modes (numeric, alphanumeric, byte/binary, and kanji) to efficiently store data. For example, the receipt identifies a specific restaurant or business and transaction that physical activity and dietary service program 200 associates with a specific individual. Physical activity and dietary service program 200 utilizes the receipt information to access restaurant device 160, grocery device 170, and/or vendor device 190 to identify the selection of meal recommendation 122 and/or the redemption of retailer offer 124. Physical activity and dietary service program 200 utilizes the transaction number to access receipt data within restaurant device 160, which provides details pertaining to purchases of meal recommendation 122 and/or purchases of physical good and/or services. Physical activity and dietary service program 200 identifies retailer offers (e.g., special pricing, promotions, redeemed coupon codes, redeemed offers, discounts, amount saved, etc.) that are noted within the receipt. For purchases of meal recommendation 122, physical activity and dietary service program 200 retrieves caloric and nutritional content information from menu information 166. Physical activity and dietary service program 200 stores the user selection of meal recommendation 122 and/or redeemed instances of retailer offer 124 for further utilization (e.g., history data for subsequent iterations and tracking or purchases, tracking calorie consumption, etc.).

In another embodiment, physical activity and dietary service program 200 on restaurant device 160 automatically adjusts an item ordered by the individual (e.g., meal recommendation 122. Physical activity and dietary service program 200 analyzes the selected instance of meal recommendation 122 with respect to nutritional content, the remaining number of allowed calories for consumption, dietary plan 118 and/or physical activity data 119. Physical activity and dietary service program 200 identifies automatic additions and/or substitutions (e.g., additional food item and/or food substitution) to meal recommendation 122 based on the analysis to fulfill and/or to come closer to achieving nutritional content and the remaining number of allowed calories (i.e., retrieves calorie and nutritional content information associated with the automatic additions and/or substitutions to ensure the addition and/or substitution does not exceed the remaining number of allowed calories), for consumption, while maintaining dietary plan 118 and accounting for physical activity (e.g., requests changes to meal recommendation 122 content that aid in physical recovery of the individual after a workout). Physical activity and dietary service program 200 automatically updates meal recommendation 122 with the identified additional food item and/or substitutions. Physical activity and dietary service program 200 recalculates the remaining number of allowed calories and the nutritional content to include the additional food item and/or substitutions.

For example, an individual orders a chef salad based on meal recommendation 122, which is a lettuce salad and/or other leaf vegetables that includes hard boiled eggs, ham, turkey, tomatoes, cucumbers, and cheese. A chef salad contains 200 calories, 10 g of fat, 235 mg of sodium, 95 mg of potassium, 29 g of carbohydrates, 2 g of sugar, and 9 g of protein. Within dietary plan 118, the user identifies, a low sodium diet due to high blood pressure, and physical activity data identifies the individual just completed a weight lifting routine. Physical activity and dietary service program 200 based on tracking of prior food consumption and dietary plan 118, identifies that the individual is approaching a limit on sodium intake, and that the user should ingest another 8 g of protein to build muscle and to aid in recovery. Physical activity and dietary service program 200 automatically updates the order for the individual to add an additional hardboiled egg, which adds 77 calories and 6.26 g of protein to the chef salad, which does not exceed the number of remaining calories allowed of 300. In addition, physical activity and dietary service program 200 automatically requests an update to the chef salad to replace the regular sliced ham, which includes 730 mg of sodium, with low sodium ham, which includes 460 mg of sodium, or sliced turkey ham, which includes 218 mg of sodium to stay within the low sodium diet limits. However, if the restaurant does not have low sodium ham or turkey ham, physical activity and dietary service program 200 updates the order to increase the amount of sliced turkey, which includes 288 mg of sodium, and reduce the amount of ham on the salad, such that the combination of ham and turkey does not exceed the allowable amount of sodium identified by the low sodium diet.

In step 218, physical activity and dietary service program 200 tracks user selection of meal recommendation 122 and/or redeemed instances of retailer offer 124. Physical activity and dietary service program 200 adjusts the overall number of calories for consumption by the number of calories consumed in meal recommendation 122 to calculate a remaining number of allowed calories for consumption. Additionally, in some embodiments, physical activity and dietary service program 200 adjusts the remaining amounts of the types of fuel to consume based on meal recommendation 122 and dietary plan 118 (i.e., determines the remaining nutritional content to consume within a specified time period to maintain dietary plan 118). For example, physical activity and dietary service program 200 calculates that the individual is allowed to eat 2,000 calories in a day in which 1200 calories are from carbohydrates, 200 calories are from protein, and 600 calories are from fats. At breakfast the user selects meal recommendation 122, which is the breakfast sandwich, which contains 300 total calories, 12 g of fat, 29 g of carbohydrates, and 18 g of protein. Physical activity and dietary service program 200 retrieves the amount of fuel types to consume (e.g., 67 g of fat, 290 g of carbohydrates, 50 g of protein, and) within dietary plan 118. Physical activity and dietary service program 200 determines the individual may consume an additional 1700 calories (e.g., remaining number of allowed calories for consumption) comprised of 55 g of fat, 261 g of carbohydrates, and 42 g of protein (e.g., remaining nutritional content).

Additionally, if physical activity and dietary service program 200 determines the user redeemed retailer offer 124, physical activity and dietary service program 200 stores the details of the purchase (e.g., identifies items, products, services purchased, quantity or number of each item purchased, purchase price of each item, etc.) and retailer offer 124 for further use. Physical activity and dietary service program 200 tracks the value or type of retailer offer 124 (e.g., size of the discount, percentage of a purchase, flat rate monetary reduction, buy one get one promotion, etc.) as history data. Additionally, physical activity and dietary service program 200 stores the item purchased (e.g., a service, a good, a product, a food item, clothing, shoes, etc.) in the history data. For example, the individual visits a gym and is not a member. The individual receives retailer offer 124 that offer the individual the opportunity to purchase a three month gym membership, regularly prices at $150 for the price of two months or $100. Upon redeeming retailer offer 124, physical activity and dietary service program 200 stores the length of the membership (e.g., 3 months) and the price paid (e.g., $100).

Upon completion, physical activity and dietary service program 200 returns to track user activity and exercise level (step 204). In subsequent iterations, while physical activity and dietary service program 200 determines the time period (e.g., a day, a set number of hours, time between a meal and a snack, time between meals, etc.) is valid, physical activity and dietary service program 200 utilizes the remaining number of allowed calories for consumption and/or the remaining amounts of the types of fuel to consume to determine meal recommendation 122 to maintain dietary plan 118 or dietary plan 148. For example, a time period is the time of one calendar day. At the end of the calendar day, physical activity and dietary service program 200 resets the values for calorie consumption and the amounts of each type of fuel to consume based on daily requirements. In another example, physical activity and dietary service program 200 sets the calories for consumption and each type of fuel to consume based on dietary plan 118 for each specified time period.

Additionally, in subsequent iterations, physical activity and dietary service program 200 utilizes the tracking information (e.g., history data, trends, etc.) to generate additionally instances of retailer offer 124 on a subsequent visit to the business by the individual. Physical activity and dietary service program 200 created additional instances of retailer offer 124 based on the previously purchased item and/or the value of the redeemed instance of retailer offer 124. In another embodiment, physical activity and dietary service program 200 utilizes the tracking information to generate instances of retailer offer 124 for future redemption by the individual to encourage the individual to return to the business. For example, physical activity and dietary service program 200 sends retailer offer 124 to client device 110 immediately after the sale for near term redemption (e.g., today, within 2 weeks of purchase, etc.) In another example, physical activity and dietary service program 200 sends an instance of retailer offer 124 to the individual after physical activity and dietary service program 200 determines the individual has not returned to the business within a period of time (e.g., 2 weeks, 1 month, 6 weeks, etc.) to encourage the individual to return to the business.

Figure 3:
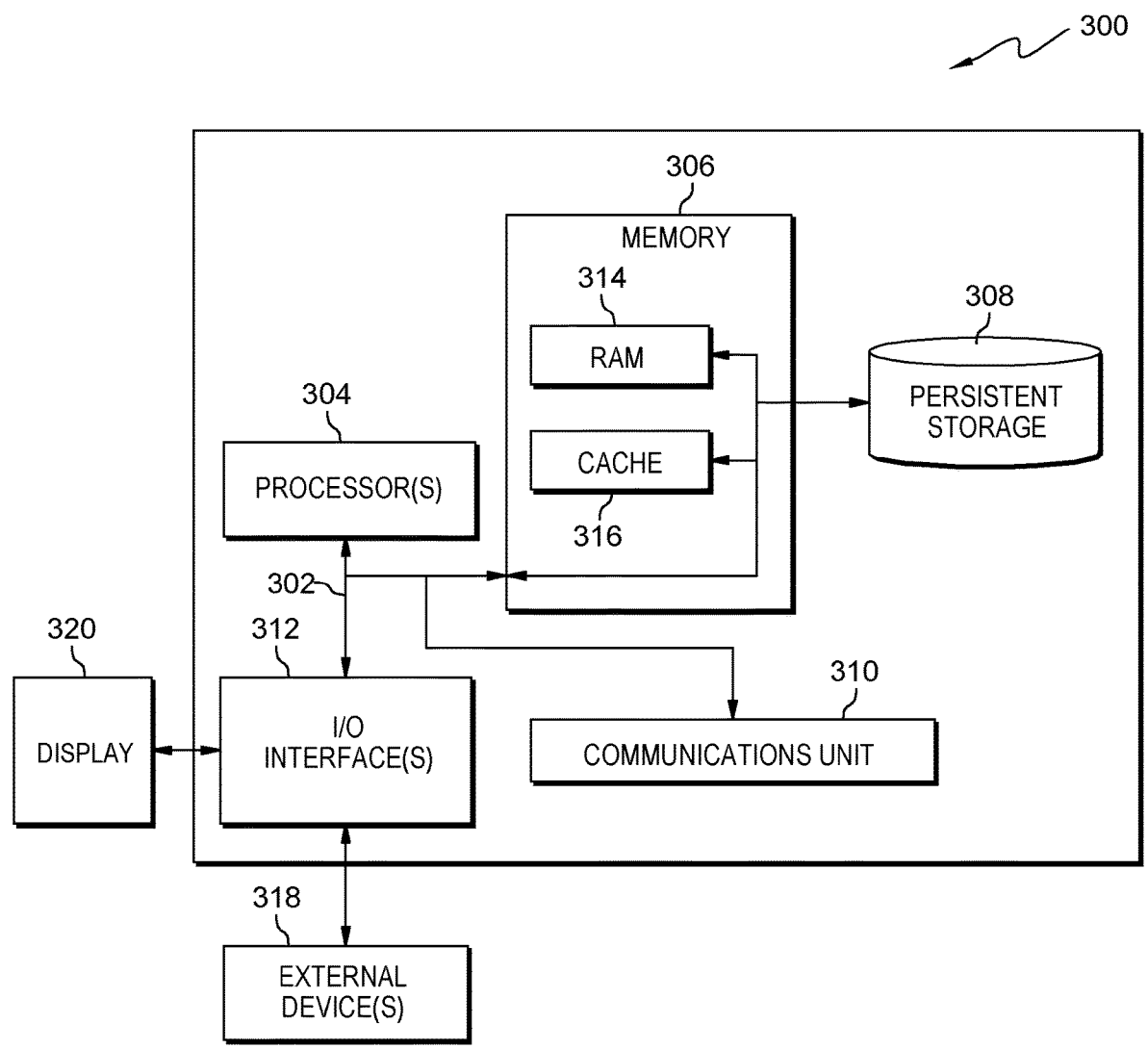
FIG. 3 is a block diagram of components of the server executing the physical activity and dietary service program, in accordance with an embodiment of the present invention.

FIG. 3 depicts a block diagram of components of server in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Server 300 includes communications fabric 302, which provides communications between cache 316, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses or a crossbar switch.

Memory 306 and persistent storage 308 are computer readable storage media. In this embodiment, memory 306 includes random access memory (RAM) 314. In general, memory 306 can include any suitable volatile or non-volatile computer readable storage media. Cache 316 is a fast memory that enhances the performance of computer processor(s) 304 by holding recently accessed data, and data near accessed data, from memory 306.

User interface 112, user interface 142, user interface 152, user interface 162, user interface 182, physical activity and dietary service client program 114, physical activity and dietary service client program 144, physical activity and dietary service client program 154, physical activity and dietary service client program 164, physical activity and dietary service client program 174, physical activity and dietary service client program 184, physical activity and dietary service client program 194, user information 116, user information 146, user information 156, dietary plan 118, dietary plan 148, physical activity data 119, physical activity data 149, physical activity data 159, shopping list 117, meal recommendation 122, retailer offer 124, menu information 166, store inventory 172, merchandise inventory 192, and physical activity and dietary service program 200 may be stored in persistent storage 308 and in memory 306 for execution and/or access by one or more of the respective computer processor(s) 304 via cache 316. In an embodiment, persistent storage 308 includes a magnetic hard disk drive. Alternatively, or in addition to a magnetic hard disk drive, persistent storage 308 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of persistent storage 308.

Communications unit 310, in these examples, provides for communications with other data processing systems or devices. In these examples, communications unit 310 includes one or more network interface cards. Communications unit 310 may provide communications through the use of either or both physical and wireless communications links. User interface 112, user interface 142, user interface 152, user interface 162, user interface 182, physical activity and dietary service client program 114, physical activity and dietary service client program 144, physical activity and dietary service client program 154, physical activity and dietary service client program 164, physical activity and dietary service client program 174, physical activity and dietary service client program 184, physical activity and dietary service client program 194, user information 116, user information 146, user information 156, dietary plan 118, dietary plan 148, physical activity data 119, physical activity data 149, physical activity data 159, shopping list 117, meal recommendation 122, retailer offer 124, menu information 166, store inventory 172, merchandise inventory 192, and physical activity and dietary service program 200 may be downloaded to persistent storage 308 through communications unit 310.

I/O interface(s) 312 allows for input and output of data with other devices that may be connected to server 300. For example, I/O interface(s) 312 may provide a connection to external device(s) 318, such as a keyboard, a keypad, a touch screen, and/or some other suitable input device. External devices 318 can also include portable computer readable storage media such as, for example, thumb drives, portable optical or magnetic disks, and memory cards. Software and data used to practice embodiments of the present invention, e.g., user interface 112, user interface 142, user interface 152, user interface 162, user interface 182, physical activity and dietary service client program 114, physical activity and dietary service client program 144, physical activity and dietary service client program 154, physical activity and dietary service client program 164, physical activity and dietary service client program 174, physical activity and dietary service client program 184, physical activity and dietary service client program 194, user information 116, user information 146, user information 156, dietary plan 118, dietary plan 148, physical activity data 119, physical activity data 149, physical activity data 159, shopping list 117, meal recommendation 122, retailer offer 124, menu information 166, store inventory 172, merchandise inventory 192, and physical activity and dietary service program 200, can be stored on such portable computer readable storage media and can be loaded onto persistent storage 308 via I/O interface(s) 312. I/O interface(s) 312 also connect to a display 320.

Display 320 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for providing dynamic services, the method comprising:
   receiving, by one or more computer processors, a first dietary plan for an individual from a fitness tracking device;
   tracking, by the one or more computer processors, a physical activity data for the individual from the fitness tracking device, wherein the fitness tracking device incorporates accelerometers, altimeters, and gyroscopes to track distance, heartbeat, quality of sleep, type of activity, and length of activity;

calculating, by the one or more computer processors, a calorie expenditure for the individual based on the physical activity data from the fitness tracking device;

graphing, by the one or more computer processors, the physical activity data on the fitness tracking device;

determining, by the one or more computer processors, whether the individual is at a store, wherein whether the individual is at the store is determined from a global positioning system in the fitness tracking device;

responsive to determining that the individual is at the store, accessing, by the one or more computer processors, an inventory for the store;

identifying, by the one or more computer processors, one or more items for purchase by the individual from the inventory for the store based on the first dietary plan and the physical activity data;

calculating, by the one or more computer processors, an elapsed time, wherein the elapsed time is an actual amount of time between a completion of a workout within the physical activity data and a time of arrival at the store;

determining, by the one or more computer processors, whether the elapsed time is within a defined period of time that identifies a time prior to and after the workout;

responsive to determining that the physical activity occurs within the defined period of time, creating, by the one or more computer processors, a second dietary plan;

creating, by the one or more computer processors, one or more meal recommendations for the individual based at least in part on the first dietary plan, the physical activity data, the one or more items for purchase by the individual within the inventory for the store, and the second dietary plan;

providing, by the one or more computer processors, the one or more meal recommendations to the individual;

receiving, by the one or more computer processors, a selection from the one or more meal recommendations; and tracking, by the one or more computer processors, the selection from the one or more meal recommendations on the physical fitness tracking device.

2. The method of claim 1, wherein creating the one or more meal recommendations for the individual based at least in part on the first dietary plan, the physical activity data, the one or more items for purchase by the individual within the inventory for the store, and the second dietary plan further comprises:

determining, by the one or more computer processors, whether the individual is at a restaurant, wherein whether the individual is at the restaurant is determined from the global positioning system in the fitness tracking device;

responsive to determining that the individual is at the restaurant, determining, by the one or more computer processors, a total number of calories for consumption based at least in part on the first dietary plan, the physical activity data, the one or more items for purchase by the individual within the inventory for the store, and the second dietary plan;

retrieving, by the one or more computer processors, a menu information associated with the restaurant, wherein the menu information includes a caloric value of the menu information and the one or more meal recommendations of one or more menu items;

identifying, by the one or more computer processors, one or more meal options based on a comparison of the caloric value of the menu information and the total number of calories for consumption;

identifying, by the one or more computer processors, a consumption nutritional content based at least in part on the first dietary plan, wherein the consumption nutritional content includes at least one of a percentage of carbohydrates, fats, and protein for consumption; and creating, by the one or more computer processors, the one or more meal recommendations from within the one or more meal options based on a comparison of a meal options nutritional content to the consumption nutritional content.

3. The method of claim 2, further comprising:

analyzing, by the one or more computer processors, a meal recommendations nutritional content of the one or more meal recommendations, with respect to a total number of remaining calories for consumption and a remaining nutritional content;

identifying, by the one or more computer processors, an additional food item to add to the one or more meal recommendations;

retrieving, by the one or more computer processors, a caloric value of the additional food item;

retrieving, by the one or more computer processors, an additional item nutritional content of the additional food item;

recalculating, by the one or more computer processors, the total number of remaining calories for consumption based on the caloric value of the additional food item; and recalculating, by the one or more computer processors, the remaining nutritional content based on the additional item nutritional content of the additional food item.

4. The method of claim 1, wherein tracking the selection from the one or more meal recommendations further comprises:

determining, by the one or more computer processors, whether the selection is a meal recommendation of the one or more meal recommendations;

responsive to determining that the selection is the meal recommendation, identifying, by the one or more computer processors, the meal recommendation within a menu information;

retrieving, by the one or more computer processors, a caloric value of the meal recommendation within the menu information;

retrieving, by the one or more computer processors, a meal recommendations nutritional content within the menu information;

calculating, by the one or more computer processors, a total number of remaining calories for consumption based on the caloric value of the meal recommendation within the menu information; and calculating, by the one or more computer processors, a remaining nutritional content for consumption based on the meal recommendations nutritional content within the menu information.

5. The method of claim 1, wherein tracking the selection from the one or more meal recommendations further comprises:

determining, by the one or more computer processors, whether the selection is a retailer offer;

responsive to determining that the selection is the retailer offer, identifying, by the one or more computer processors, a purchase item;

identifying, by the one or more computer processors, a value of the retailer offer associated with the purchase item; and storing, by the one or more computer processors, the value of the retailer offer and the purchase item.

6. A computer program product for providing dynamic services, the computer program product comprising:

one or more computer readable storage media and program instructions stored on the one or more computer readable storage media, the program instructions including instructions to:

receive a first dietary plan for an individual from a fitness tracking device;

track a physical activity data for the individual from the fitness tracking device, wherein the fitness tracking device incorporates accelerometers, altimeters, and gyroscopes to track distance, heartbeat, quality of sleep, type of activity, and length of activity;

calculate a calorie expenditure for the individual based on the physical activity data from the fitness tracking device;

graph the physical activity data on the fitness tracking device;

determine whether the individual is at a store, wherein whether the individual is at the store is determined from a global positioning system in the fitness tracking device;

responsive to determining that the individual is at the store, access an inventory for the store;

identify one or more items for purchase by the individual from the inventory for the store based on the first dietary plan and the physical activity data;

calculate an elapsed time, wherein the elapsed time is an actual amount of time between a completion of a workout within the physical activity data and a time of arrival at the store;

determine whether the elapsed time is within a defined period of time that identifies a time prior to and after the workout;

responsive to determining that the physical activity occurs within the defined period of time, create a second dietary plan;

create one or more meal recommendations for the individual based at least in part on the first dietary plan, the physical activity data, the one or more items for purchase by the individual within the inventory for the store, and the second dietary plan;

provide the one or more meal recommendations to the individual;

receive a selection from the one or more meal recommendations; and track the selection from the one or more meal recommendations on the fitness tracking device.

7. The computer program product of claim 6, wherein creating the one or more meal recommendations for the individual based at least in part on the first dietary plan, the physical activity data, the one or more items for purchase by the individual within the inventory for the store, and the second dietary plan further comprises:

determining whether the individual is at a restaurant, wherein whether the individual is at the restaurant is determined from the global positioning system in the fitness tracking device;

responsive to determining that the individual is at the restaurant, determining a total number of calories for consumption based at least in part on the first dietary plan, the physical activity data, the one or more items for purchase by the individual within the inventory for the store, and the second dietary plan;

retrieving a menu information associated with the restaurant, wherein the menu information includes a caloric value of the menu information and one or more meal recommendations of one or more menu items;

identifying one or more meal options based on a comparison of the caloric value of the menu information and the total number of calories for consumption;

identifying a consumption nutritional content based at least in part on the first dietary plan, wherein the consumption nutritional content includes at least one of a percentage of carbohydrates, fats, and protein for consumption; and creating the one or more meal recommendations from within the one or more meal options based on a comparison of a meal options nutritional content to the consumption nutritional content.

8. The computer program product of claim 7, further comprising:

analyzing a meal recommendations nutritional content of the one or more meal recommendations, with respect to a total number of remaining calories for consumption and a remaining nutritional content;

identifying an additional food item to add to the one or more meal recommendations;

retrieving a caloric value of the additional food item;

retrieving an additional item nutritional content of the additional food item;

recalculating the total number of remaining calories for consumption based on the caloric value of the additional food item; and recalculating the remaining nutritional content based on the additional item nutritional content of the additional food item.

9. The computer program product of claim 6, wherein tracking the selection from the one or more meal recommendations further comprises:

determining whether the selection is a meal recommendation of the one or more meal recommendations;

responsive to determining that the selection is the meal recommendation, identifying the meal recommendation within a menu information;

retrieving a caloric value of the meal recommendation within the menu information;

retrieving a meal recommendations nutritional content within the menu information;

calculating a total number of remaining calories for consumption based on the caloric value of the meal recommendation within the menu information; and calculating a remaining nutritional content for consumption based on the meal recommendations nutritional content within the menu information.

10. The computer program product of claim 6, wherein tracking the selection from the one or more meal recommendations further comprises:

determining whether the selection is a retailer offer;

responsive to determining that the selection is the retailer offer, identifying a purchase item;

identifying a value of the retailer offer associated with the purchase item; and storing the value of the retailer offer and the purchase item.

11. A computer system for providing dynamic services, the computer system comprising:
- one or more computer processors, one or more computer readable storage media, and program instructions stored on the computer readable storage media for execution by at least one of the one or more processors, the program instructions including instructions to:
- receive a first dietary plan for an individual from a fitness tracking device;
- track a physical activity data for the individual from the fitness tracking device, wherein the fitness tracking device incorporates accelerometers, altimeters, and gyroscopes to track distance, heartbeat, quality of sleep, type of activity, and length of activity;
- calculate a calorie expenditure for the individual based on the physical activity data from the fitness tracking device;
- graph the physical activity data on the fitness tracking device;
- determine whether the individual is at a store, wherein whether the individual is at the store is determined from a global positioning system in the fitness tracking device;
- responsive to determining that the individual is at the store, access an inventory for the store;
- identify one or more items for purchase by the individual from the inventory for the store based or the first dietary plan and the physical activity data;
- calculate an elapsed time, wherein the elapsed time is an actual amount of time between a completion of a workout within the physical activity data and a time of arrival at the store;
- determine whether the elapsed time is within a defined period of time that identifies a time prior to and after the workout;
- responsive to determining that the physical activity occurs within the defined period of time, create a second dietary plan;
- create one or more meal recommendations for the individual based at least in part on the first dietary plan, the physical activity data, the one or more items for purchase by the individual within the inventory for the store, and the second dietary plan;
- provide the one or more meal recommendations to the individual;
- receive a selection from the one or more meal recommendations; and
- track the selection from the one or more meal recommendations on the fitness tracking device.

12. The computer system of claim 11, wherein creating the one or more meal recommendations for the individual based at least in part on the first dietary plan, the physical activity data, the one or more items for purchase by the individual within the inventory for the store, and the second dietary plan-further comprises:
- determining whether the individual is at a restaurant, wherein whether the individual is at the restaurant is determined from the global positioning system in the fitness tracking device;
- responsive to determining that the individual is at the restaurant, determining a total number of calories for consumption based at least in part on the first dietary plan, the physical activity data, the one or more items for purchase by the individual within the inventory for the store, and the second dietary plan;
- retrieving a menu information associated with the restaurant, wherein the menu information includes a caloric value of the menu information and one or more meal recommendations of one or more menu items;
- identifying one or more meal options based on a comparison of the caloric value of the menu information and the total number of calories for consumption;
- identifying a consumption nutritional content based at least in part on the first dietary plan, wherein the consumption nutritional content includes at least one of a percentage of carbohydrates, fats, and protein for consumption; and
- creating the one or more meal recommendations from within the one or more meal options based on a comparison of a meal options nutritional content to the consumption nutritional content.

13. The computer system of claim 12, further comprising:
- analyzing a meal recommendations nutritional content of the one or more meal recommendations, with respect to a total number of remaining calories for consumption and a remaining nutritional content;
- identifying an additional food item to add to the one or more meal recommendations;
- retrieving a caloric value of the additional food item;
- retrieving an additional item nutritional content of the additional food item;
- recalculating the total number of remaining calories for consumption based on the caloric value of the additional food item; and
- recalculating the remaining nutritional content based on the additional item nutritional content of the additional food item.

14. The computer system of claim 11, wherein tracking the selection from the one or more meal recommendations further comprises:
- determining whether the selection is a meal recommendation of the one or more meal recommendations;
- responsive to determining that the selection is the meal recommendation, identifying the meal recommendation within a menu information;
- retrieving a caloric value of the meal recommendation within the menu information;
- retrieving a meal recommendations nutritional content within the menu information;
- calculating a total number of remaining calories for consumption based on the caloric value of the meal recommendation within the menu information; and
- calculating a remaining nutritional content for consumption based on the meal recommendations nutritional content within the menu information.

* * * * *